United States Patent
Ramji et al.

(10) Patent No.: US 12,416,002 B2
(45) Date of Patent: Sep. 16, 2025

(54) ANALYSIS SYSTEM FOR ORTHOGONAL ACCESS TO AND TAGGING OF BIOMOLECULES IN CELLULAR COMPARTMENTS

(71) Applicant: ILLUMINA, INC., San Diego, CA (US)

(72) Inventors: Ramesh Ramji, San Diego, CA (US); Frank J. Steemers, San Diego, CA (US); Lena Christiansen, San Diego, CA (US); Dmitry K. Pokholok, San Diego, CA (US); Fan Zhang, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 916 days.

(21) Appl. No.: 16/456,763

(22) Filed: Jun. 28, 2019

(65) Prior Publication Data

US 2019/0323003 A1    Oct. 24, 2019

Related U.S. Application Data

(63) Continuation of application No. PCT/US2017/068672, filed on Dec. 28, 2017.

(60) Provisional application No. 62/440,089, filed on Dec. 29, 2016.

(51) Int. Cl.
   *C12N 15/10* (2006.01)
   *C12N 9/12* (2006.01)
   *C12N 9/22* (2006.01)

(52) U.S. Cl.
   CPC ....... *C12N 15/1065* (2013.01); *C12N 9/1252* (2013.01); *C12N 9/22* (2013.01); *C12N 15/1068* (2013.01); *C12N 15/1089* (2013.01)

(58) Field of Classification Search
   CPC .................................................... C12N 15/10
   See application file for complete search history.

(56) References Cited

U.S. PATENT DOCUMENTS

| | | |
|---|---|---|
| 6,654,696 B1 | 11/2003 | Davies |
| 7,574,305 B2 | 8/2009 | Seul et al. |
| 2006/0134629 A1 | 6/2006 | Link et al. |
| 2010/0120098 A1 | 5/2010 | Grunenwald et al. |
| 2010/0323348 A1 | 12/2010 | Hamady et al. |
| 2012/0208705 A1 | 8/2012 | Steemers et al. |
| 2012/0208724 A1 | 8/2012 | Steemers et al. |
| 2012/0316074 A1* | 12/2012 | Saxonov ............... C12N 15/10 506/26 |
| 2014/0194324 A1 | 7/2014 | Gormley et al. |
| 2016/0060691 A1* | 3/2016 | Giresi .................. C12Q 1/6869 506/7 |

FOREIGN PATENT DOCUMENTS

| | | |
|---|---|---|
| RU | 2464315 C2 | 10/2012 |
| WO | 2007109035 A2 | 9/2007 |
| WO | 2010062913 A2 | 6/2010 |
| WO | 2012048341 A1 | 4/2012 |
| WO | 2012061832 A1 | 5/2012 |
| WO | 2012108864 A1 | 8/2012 |
| WO | 2014142850 A1 | 9/2014 |
| WO | 2014189957 | 11/2014 |
| WO | 2015200609 | 12/2015 |
| WO | 2016073690 | 5/2016 |
| WO | 2016130704 | 8/2016 |

OTHER PUBLICATIONS

Kia et al., Improved Genome Sequencing Using an Engineered Transposase, BMC Biotechnology, 2017, 17(6), 1-10. (Year: 2017).*
Boni et al., Live Imaging and Modeling of Inner Nuclear Membrane Targeting Reveals Its Molecular Requirements in Mammalian Cells, The Journal of Cell Biology, 2015, 209(5), 705-720. (Year: 2015).*
Cusanovich et al., Multiplex Single-Cell Profiling of Chromatin Accessibility by Combinatorial Cellular Indexing, Science, published May 2015, 910-914; 2015, 1-34. (Year: 2015).*
Cusanovich et al., Multiplex Single-Cell Profiling of Chromatin Accessibility by Combinatorial Cellular Indexing, Supplementary Materials, Science, published May 2015, 2015, 1-34. (Year: 2015).*
Liashkovich et al., Clathrin Inhibitor Pitstop-2 Disrupts The Nuclear Pore Complex Permeability Barrier, Scientific Reports, 2014, 1-9 . (Year: 2014).*
Chen et al., Inhibitors of Clathrin-Dependent Endocytosis Enhance TGFbeta Signaling and Responses, Journal of Cell Science, 2009, 122(11), 1863-1873). (Year: 2009).*
Kenneally, C., Kirk-Othmer Encyclopedia of Chemical Technology, 2000, vol. 2; John Wiley & Sons. Obtained online at: https://www.wiley.com/enus/Kirk+Othmer+Encyclopedia+of+Chemical+Technology%2C+27+Volume+Set%2C+27+Volume+Set%2C+5th+Edition-p-9780471484943 on Dec. 6, 2022. (Year: 2000).*
Ash et al., The Handbook of Industrial Surfactants, 2010, vol. 1, 1-2. (Year: 2010).*
LGC, Analytical Reference Materials, Standards, and High Purity Solvents, LGC Standards, 2011, 1-988. (Year: 2011).*
Farn, R., Chemistry and Technology Surfactants, 2006, 1-331. (Year: 2006).*
Willaims, M., The Merck Index: An Encyclopedia of Chemicals, Drugs, and Biologicals, 2013, 1-3. Obtained online at: The Merck Index: An Encyclopedia of Chemicals, Drugs, and Biologicals, 15th Edition Edited by M.J. O'Neil , Royal Society of Chemistry, Cambridge, UK ISBN 9 on Dec. 7, 2022. (Year: 2013).*

(Continued)

*Primary Examiner* — Amy M Bunker
(74) *Attorney, Agent, or Firm* — Illumina, Inc.

(57) ABSTRACT

The invention relates to a system and methods for enhancing access to nuclear informational molecules, such as DNA, RNA, and proteins, by analytical biomolecules, such as transposome complexes, by treating nuclei with a nuclear permeability enhancer, and to methods of using nuclear membrane, cell membrane, and external compartmentalization approaches as contiguity preserving elements.

5 Claims, 14 Drawing Sheets
Specification includes a Sequence Listing.

(56) References Cited

OTHER PUBLICATIONS

Sigma-Aldrich, Aldrich Chemistry 2012-2014: Handbook of Fine Chemicals; Sigma-Aldrich Corporation, 2011, 1. Obtained at: Aldrich Chemistry 2012-2014: Handbook of Fine Chemicals—Sigma-Aldrich Corporation—Google Books on Dec. 7, 2022. (Year: 2011).*
Amidzadeh et al., Assessment of Different Permeabilization Methods of Minimizing Damage to the Adherent Cells for Detection of Intracellular RNA by Flow Cytometry, Avicenna J Med Biotech, 2014, 6(1), 38-46. (Year: 2014).*
Walev et al., Delivery of Proteins Into Living Cells by Reversible Membrane Permeabilization with Streptolysin-O, PNAS, 2001, 98(6), 3185-3190. (Year: 2001).*
Irvin et al., Tri(hydroxymethyl)aminomethane Buffer Modification of *Escherichia coli* Outer Membrane Permeability, Journal of Bacteriology, 1981, 1397-1403. (Year: 1981).*
Mansure, M., Changed in Cell Membrane Permeability and Lipid Content of Wheat Root Cortex Cells Induced by NaCl, Biologia Plantarum, 1995, 37(1), 143-145. (Year: 1995).*
Kojima et al., High Salt Concentrations Increase Permeability Through OmpC Channels of *Escherichia coli*, The Journal of Biological Chemistry, 2014, 289(38), 26464-26473. (Year: 2014).*
Serdiuk et al., Trypsinization-Dependent Cell Labeling With Fluorescent Nanoparticles, Nanoscale Research Letters, 2014, 9(568), 1-5. (Year: 2014).*
Ribbeck et al., The Permeability Barrier of Nuclear Pore Complexes Appears to Operate Via Hydrophobic Exclusion, The EMBO Journal, 2002, 21(11), 2664-2671. (Year: 2002).*
Patel et al., Natively Unfolded Nucleoporins Gate Protein Diffusion Across the Nuclear Pore Complex, Cell, 2007, 129, 83-96. (Year : 2007).*
Kroschwald et al., Promiscuous Interactions and Protein Disaggregases Determine the Material State of Stress-Inducible RNP Granuales, eLIFE, 2015, 4, 1-32. (Year: 2015).*
Griesenbach et al., Assessment of the Nuclear Pore Dilating Agent Trans-Cyclohexane-1,2-Diol in Differentiated Airway Epithelium, The Journal of Gene Medicine, 2012, 14, 491-500. (Year: 2012).*
Weis, Karsten, Regulating Access to the Genome: Nucleocytoplasmic Transport Throughout the Cell Cycle, Cell, 2003, 112, 441- 451. (Year: 2003).*
Makio et al., The Nucleoporins Nup170p and Nup157p are Essential for Nuclear Pore Complex Assembly, The Journal of Cell Biology, 2009, 185(3), 459-473. (Year: 2009).*
Amidzadeh et al., Assessment of Different Permeabilization Methods of Minimizing Damage to the Adherent Cells for Detection of Intracellular RNA by Flow Cytometry, Avicenna Journal of Medical Biotechnology, 2014, 6(1), 38-46. (Year: 2014).*
Skene et al., CUT & RUN: Targeted In Situ Genome-Wide Profiling with High Efficiency for Low Cell Numbers., Howard Hughes Medical Institute, 2017, 1-28. (Year: 2017).*
Naumann et al., Tn5 Transposase Active Site Mutants, Journal of Biological Chemistry, 2002, 277(20); 17623-17269. (Year: 2002).*
Lentacker et al., New Strategies For Nucleic Acid Delivery to Conquer Cellular and Nuclear Membranes, Journal of Controlled Release, 2008, 132, 279-288. (Year: 2008).*
Liashkovich et al., Exceptional Structural and Mechanical Flexibility of the Nuclear Pore Complex, Journal of Cellular Physiology, 2011, 226, 675-682. (Year: 2011).*
Naumann et al., Tn5 Transposase Active Site Mutants, The Journal of Biological Chemistry, 2002, 277(20), 17623-17629. (Year: 2002).*
Decision to Grant issued Mar. 10, 2022 in Russian Application No. 2019123065.
Search Report and Written Opinion—Corresponding PCT Application No. PCT/US2017/068672, dated Apr. 9, 2018, 12 pages.
Adam et al., "Nuclear Protein Import in Permeabilized Mammalian Cells Requires Soluble Cytoplasmic Factors," The Journal of Cell Biology, 1990, 111(3): 807-816.
BD Editors, "What Happens to a Cell in a Hypotonic Solution," Biology Dictionary, 2018 (2 pages).
Chelsky et al., "Sequence Requirements for Synthetic Peptide-Mediated Translocation to the Nucleus," Molecular and Cellular Biology, 1989, 9(6): 2487-2492.
Chen et al., "Inhibitors of Clathrin-Dependent Endocytosis Enhance TGFβ Signaling and Responses," J Cell Sci., 2009, 122(11): 1863-1871.
Dingwall et al., "The Nucleoplasmin Nuclear Location Sequence is Larger and More Complex than That of SV-40 Large T Antigen," The Journal of Cell Biology, 1998, 107(3): 841-849.
Goryshin et al., "Tn5 in Vitro Transposition," The Journal of Biological Chemistry, 1998, 273(13): 7367-7374.
Hagstrom et al., "Nuclear Import of DNA in Digitonin-Permeabilized Cells," Journal of Cell Science, 1997, 110: 2323-2331.
Hill et al., "Targeting Nucleocytoplasmic Transport in Cancer Therapy," Oncotarget, 2013, 5(1): 11-28.
Au et al., "In Vivo Genome Editing in Animals Using AAV-CRISPR System: Applications to Translational Research of Human Disease", F1000Research, 2017, 6(F1000 Faculty Rev): 2153.
Lee et al., "Rules for Nuclear Localization Sequence Recognition by Karyopherinβ2," Cell, 2006, 126(3): 543-558.
Liaskovich et al., "Clathrin Inhibitor Pitstop-2 Disrupts the Nuclear Pore Complex Permeability Barrier," Sci. Rep., 2015, 5: 09994.
Mizuuchi et al., "In Vitro Transposition of Bacteriophage Mu: A Biochemical Approach to a Novel Replication Reaction," Cell, 1983, 35(3 Pt 2): 785-794.
Moore et al., "The Two Steps of Nuclear Import, Targeting to the Nuclear Envelope and Translocation Through the Nuclear Pore, Require Different Cytosolic Factors," Cell, 1992, 69(6): 939-950.
Product Sheet, "IGEPAL® CA-630," Millipore Sigma, 2022 (8 pages).
Product Sheet, "Lysis Buffer" Bio-Rad Laboratories, Inc., 2022 (2 pages).
Product Sheet, "Sonication Lysis: Cell Disruption and Extraction," Hielscher Utrasonics GmbH, 1999 (5 pages).
Product Sheet, "What are Cationic Lipids?" BroadPharm, 2021 (2 pages).
Ray et al., "Quantitative Tracking of Protein Trafficking to the Nucleus Using Cytosolic Protein Delivery by Nanoparticle-Stabilized Nanocapsules," Biocunjug Chem, 2015, 26(6): 1004-1007.
Ribbeck et al., "The Permeability Barrier of Nuclear Pore Complexes Appears to Operate Via Hydrophobic Exclusion," The EMBO Journal, 2002, 21(11): 2664-2671.
Savilahti et al., "The Phage Mu Transpososome Core: DNA Requirements for Assembly and Function," The EMBO Journal, 1995, 14(19): 4893-4903.
Seidlmayer et al., "Inorganic Polyphosphate is a Potent Activator of the Mitochondrial Permeability Transition Pore in Cardiac Myocytes," J. Gen Physiol., 2012, 139(5): 321-31.
Tissera et al., "Nuclear Envelopes Show Cell-Type Specific Sensitivity for Permeabilization With Digitonin," Nature (Protocol Exchange), 2010, (available at https://www.nature.com/protocolexchange/protocols/1994).
Dutta et al., "Pitstop 2 Is a Potent Inhibitor of Clathrin-Independent Endocytosis," PLOS One, 012, 7(9): e45799, 1-15.
Pei et al., "Review and Inspiration of Plant Proteins Involved in the Transformation Processing of T-DNA Initiated by Agrobacterium," Scientia Agricultura Sinica, 2014, 47(13): 2504-2518 (English Abstract and English Machine Translation).
Search Report received in Chinese Application No. 201780087116. 5, dated Nov. 23, 2022, 3 pages.
Finlay et al., "Inhibition of In Vitro Nuclear Transport by a Lectin that Binds to Nuclear Pores," J Cell Biol., 1987, 104(2): 189-200.
Pandey et al., "Inhibition of nuclear pore import by a monoclonal antibody against a novel class of nuclear pore proteins," Exp Cell Res., 1994, 212(2): 243-254.
Rahmani et al., "Leptomycin B Alters the Subcellular Distribution of CRM1 (Exportin 1)," Biochem Biophys Res Commun., 2017, 488(2): 253-258.

(56) References Cited

OTHER PUBLICATIONS

Sharov et al., "Cyclosporine A attenuates mitochondrial permeability transition and improves mitochondria respiratory function in cardiomyocytes isolated from dogs with heart failure," J Mol Cell Cardiol., 2007, 42(1): 150-158.
Vaamonde-Garcia et al., "The mitochondrial inhibitor oligomycin induces an inflammatory response in the rat knee joint," BMC Musculoskelet Disord., 2017, 18: 254.
Gagarskaia et al., "Journal of Molecular Structure," 2017, 1140: 46-51 (abstract).
Product Sheet, "Fluorescein Isothiocyanate-Dextran," at www.sigmaaldrich.com/us/en/technical-documents/technical-article/cell-culture-and-cell-culture-analysis/cell-based-assays/fluorescein-isothiocyanate-dextran, downloaded on Oct. 3, 2024 (6 pages).

* cited by examiner

Figure 9

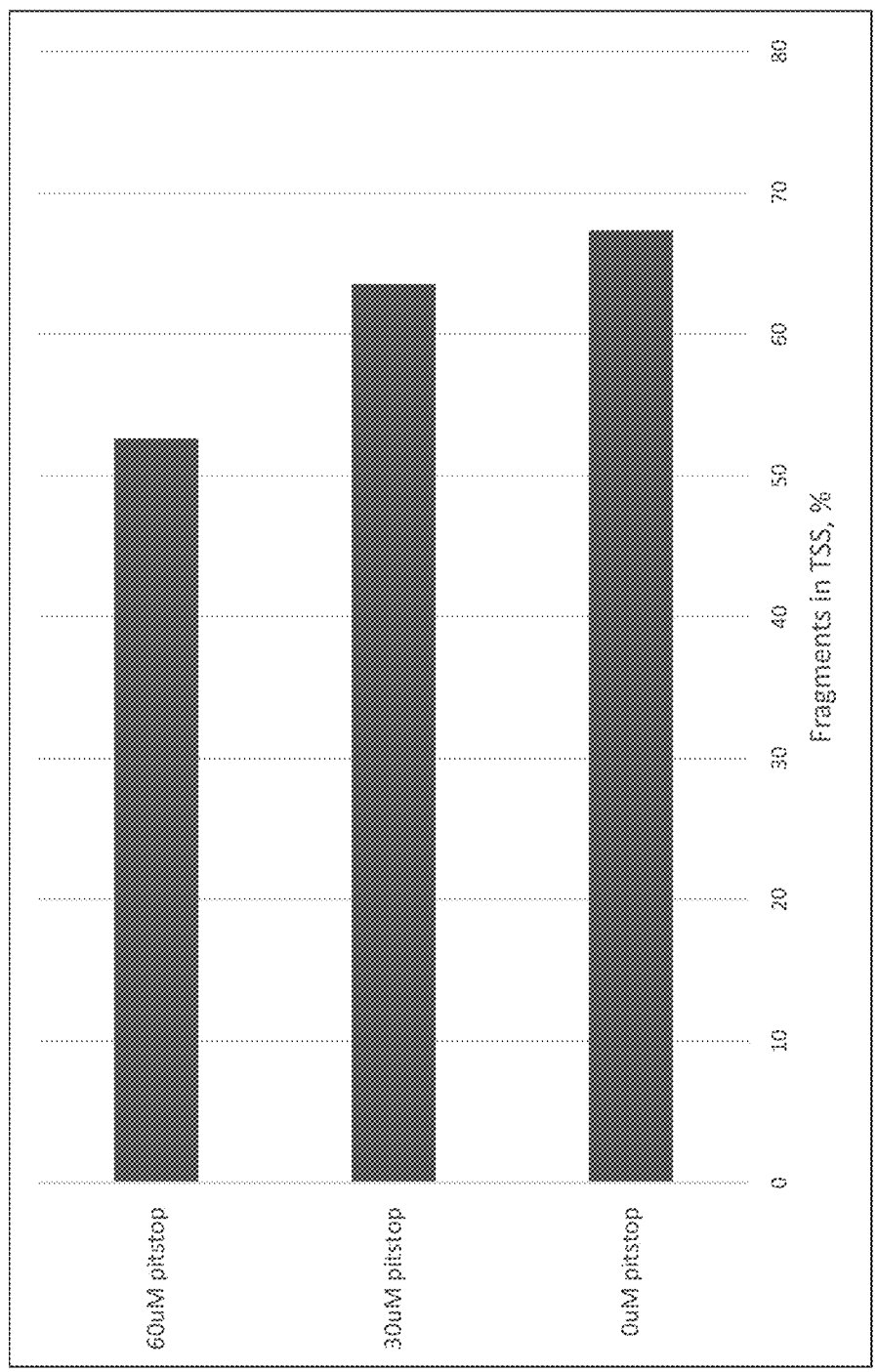

ANALYSIS SYSTEM FOR ORTHOGONAL ACCESS TO AND TAGGING OF BIOMOLECULES IN CELLULAR COMPARTMENTS

CROSS-REFERENCE TO RELATED APPLICATIONS

This application is a continuation of International Application No. PCT/US2017/068672, filed Dec. 28, 2017, which claims the benefit of priority of U.S. Provisional Application No. 62/440,089, filed Dec. 29, 2016, the contents of each of which is incorporated by reference herein in its entirety for any purpose.

SEQUENCE LISTING

The present application is filed with a Sequence Listing in electronic format. The Sequence Listing is provided as a file entitled "2019-08-22_01243-0010-00US_Seq_List_ST25.txt" created on Aug. 22, 2019, which is 2,625 bytes in size. The information in the electronic format of the sequence listing is incorporated herein by reference in its entirety.

BACKGROUND

Detection of nucleic acids and proteins in biological samples is useful for identifying and classifying microorganisms, diagnosing infectious diseases, detecting and characterizing genetic abnormalities, identifying genetic changes associated with disease onset or progression, studying genetic susceptibility to disease, and measuring response to disease treatments.

Analysis of single cells or single nuclei, or allow for discrete analysis of cytoplasmic and nuclear compartments, offer broad insight into assessments of cell type, cell differentiation, cell status, protein synthesis and regulation, evolution, disease progression and diagnosis, and responses to disease treatment. In particular, analysis of DNA and RNA, as well as histones and other nuclear proteins, at the nucleus level can be used to do entire genome sequencing, to reveal information about quiescence states of a cell and open chromatin states, or to provide real-time information about protein regulation. Such information is useful for applications such as gene editing, cell type conversion, analysis of protein regulation, and disease therapy.

Current techniques for accessing cellular nucleic acid and protein content for subsequent analysis generally employ cell lysis methods that disrupt the cellular compartments. In some methods, lysis media such as ionic detergents are used, yielding mixtures of cytoplasmic and nuclear content and preventing resolution of molecular information between the compartments (e.g., due to cross-contamination between cytoplasmic mitochondrial DNA and nuclear DNA). Alternative lysis methods employ mild, non-ionic detergents to disrupt the cellular membrane while leaving the nuclei intact. In another approach, isolated nuclei may be disrupted with digestion enzymes such as proteases.

Next-generation sequencing (NGS) techniques routinely employ a sample or library preparation step in which genomic DNA or RNA is converted into a library of fragmented, sequenceable templates. Fragmentation of genomic DNA is a crucial step in DNA sample preparation for high-throughput sequencing. In one approach, transposome complexes are used to fragment and tag target nucleic acids. Transposases mediate the fragmentation of double-stranded DNA and ligate synthetic oligonucleotides at both ends. The appended oligonucleotides enable subsequent amplification and sequencing steps. The cellular and nuclear lysis methods discussed above are incompatible with such approaches because they degrade the enzymes (e.g., ionic detergents, digestion enzymes), or because the enzymes are unable to sufficiently penetrate intact nuclei. For example, transposome complexes, such as Nextera Tn5 (dimer~106 kDa), that are used in current tagmentation protocols are unable to access nuclear material efficiently due to the complexity of the nuclear envelope (see FIG. 1). The nuclear envelope is composed of an outer nuclear membrane and an inner nuclear membrane, which together form a lipid bilayer that restricts diffusion of biomolecules from the cytoplasm into the nucleus. Nuclear pore complexes (NPCs) span the nuclear membrane and tightly regulate transport of biomolecules in and out of the nucleus, typically allowing only molecules less than 40 kDa in size to pass through. Adjacent to the inner nuclear membrane is the nuclear lamina, which includes protein filaments, such as scaffold/matrix attachment elements, clathrin, and other proteins, that create a supportive framework to maintain nuclear rigidity and control size-selected entry of molecules into the nucleus. Because of these issues of enzymatic degradation and limited diffusion across the nuclear membrane, cell lysis methods would require additional purification and isolation steps to isolate target nucleic acids or proteins before further sample preparation could be effected.

Analysis of single cell content may be accomplished by isolating single cells in discrete compartments. In one technique, cells are distributed into water droplets in an oil medium. However, the oil impedes transfer of materials and sample preparation enzymes in and out of the aqueous droplets, so all such reagents must be present in the initial aqueous medium. Furthermore, contiguity information may be preserved using compartmentalization methods such as contiguity preserving elements (CEs) as described in PCT Publ. No. WO2016/013704. However, such techniques do not address the limitations of discussed above regarding discrete access to nuclear and cytoplasmic elements.

There is a need for sample preparation methods for analyzing cellular components, for example, by next-generation sequencing, that provide efficient access to nuclear genetic material, allow for independent detection of nuclear and cytoplasmic content, and generate suitable fragmented DNA or RNA libraries for sequencing, while maintaining cytoplasmic and nuclear compartment and/or nuclear contiguity. Discussed herein are methods that provide for sample preparation methods to be performed within the intact nucleus, in essence using the nuclear envelope as a CE.

SUMMARY

The present disclosure is directed to methods of delivering an analytical biomolecule into a cell nucleus and reacting the analytical biomolecule with a cell nucleus informational molecule (such as a nucleic acid or protein) by contacting a cell and/or cell nucleus with a nuclear permeability enhancer. In some aspects, the methods include reacting a second analytical biomolecule with a cytoplasmic informational molecule (such as a nucleic acid or protein). In some aspects, the methods include steps that facilitate analysis of individual cells and/or individual nuclei. In some aspects, a single cell and/or nucleus content is localized with a contiguity preserving element. In some aspects, multiple contiguity preserving elements are employed, allowing for independent analysis of analytes from different cellular compartments. In some aspects, the nuclear membrane serves as a contiguity preserving element, or as one of a plurality of contiguity preserving elements. Such treatment also allows for removal of large biomolecules, such as analysis complexes, from nuclei to facilitate isolation and/or analysis.

Described herein are methods of reacting a cell nucleus informational molecule with an analytical biomolecule, comprising contacting the cell nucleus with a nuclear permeability enhancer and reacting the informational molecule with the analytical biomolecule.

Described herein are methods of analyzing a cell nucleus informational molecule comprising:
- (a) contacting a cell nucleus comprising a cell nucleus informational molecule with a nuclear permeability enhancer and an analytical biomolecule;
- (b) reacting the analytical biomolecule with the cell nucleus informational molecule to provide an analysis complex; and
- (c) analyzing the analysis complex, thereby detecting the cell nucleus informational molecule.

Such methods may comprise analyzing a cytoplasmic informational molecule. Thus, the disclosure is directed to methods of analyzing a nuclear informational molecule and a cytoplasmic informational molecule comprising:
- (a) contacting a cell comprising a cell nucleus informational molecule and a cytoplasmic informational molecule with a nuclear permeability enhancer, a first analytical biomolecule, and a second analytical biomolecule;
- (b) reacting the first analytical biomolecule with the cell nucleus informational molecule to provide a first analysis complex and reacting the second analytical biomolecule with the cytoplasmic informational molecule to provide a second analysis complex;
- (c) analyzing the first analysis complex, thereby detecting the cell nucleus informational molecule; and, optionally,
- (d) analyzing the second analysis complex, thereby detecting the cytoplasmic informational molecule.

Methods described herein may make use of contiguity preserving elements. The disclosure is therefore directed to methods of analyzing a cell nucleus informational molecule comprising:
- (a) providing a contiguity preserving element comprising a nucleus, wherein the nucleus comprises a cell nucleus informational molecule;
- (b) contacting the contiguity preserving element with a nuclear permeability enhancer and an analytical biomolecule; and
- (c) reacting the analytical biomolecule with the cell nucleus informational molecule to provide an analysis complex; and
- (d) analyzing the analysis complex, thereby detecting the cell nucleus informational molecule.

The disclosure is further directed to methods of analyzing a cell nucleus informational molecule and a cytoplasmic informational molecule comprising:
- (a) providing a contiguity preserving element comprising a cell, wherein the cell comprises a cell nucleus informational molecule and a cytoplasmic informational molecule;
- (b) contacting the contiguity preserving element with a nuclear permeability enhancer, a first analytical biomolecule, and a second analytical biomolecule;
- (c) reacting the first analytical biomolecule with the cell nucleus informational molecule to provide a first analysis complex and reacting the second analytical biomolecule with the cytoplasmic informational molecule to provide a second analysis complex;
- (d) analyzing the first analysis complex, thereby detecting the cell nucleus informational molecule; and, optionally,
- (e) analyzing the second analysis complex, thereby detecting the cytoplasmic informational molecule.

In the above methods, the analytical biomolecules may be transposome complexes. Thus, described herein are methods of fragmenting and tagging target nucleic acids in a nucleus using transposome complexes and a nuclear permeability enhancer. Treating cells or cell nuclei with a nuclear permeability enhancer allows for efficient delivery of transposome complexes to the nuclear space. The disclosure is directed to methods of delivering transposases or transposome complexes into cell nuclei by treating cells or nuclei with a cell nucleus permeability enhancer. In this manner, transposition of nuclear genetic material may be effected within the nucleus.

Described herein are methods of preparing a library of tagged nucleic acid fragments from a cell nuclear target nucleic acid comprising:
- (a) contacting a cell nucleus comprising a target nucleic acid with a nuclear permeability enhancer and a plurality of transposome complexes, wherein each transposome complex comprises a transposase and two transposon end compositions comprising transposon end sequences;
- (b) reacting the target nucleic acid with the plurality of transposome complexes whereby the target nucleic acid is fragmented into double-stranded nucleic acid fragments and tagged with transferred strands from the transposon end compositions to form tagged analysis complexes; and
- (c) analyzing the tagged analysis complexes, thereby detecting the tagged nucleic acid fragments.

Also described herein are methods of preparing a library of tagged nucleic acid fragments from a cell nuclear target nucleic acid:
- (a) providing a contiguity preserving element comprising a single nucleus, wherein the single nucleus comprises a target nucleic acid;
- (b) contacting the contiguity preserving element and single nucleus with a nuclear permeability enhancer and an analytical biomolecule; and
- (c) reacting the analytical biomolecule with the cell nucleus informational molecule to provide an analysis complex; and
- (d) analyzing the analysis complex, thereby detecting the cell nucleus informational molecule.

In some methods, a contiguity preserving element comprises the cell nucleus (isolated or within a cell) with the target nucleic acid. The methods may further comprise preparing and analyzing a cytoplasmic informational molecule as discussed above.

In some embodiments, differential access to cellular, cytoplasmic, and nuclear cell components allows analysis of RNA, DNA, protein or any combination thereof from one or more cells or one or more cytoplasmic and nuclear cell components.

In some methods, compounds or biomolecules (e.g., nuclear pore blockers) are used to block access to certain cytoplasmic and nuclear compartments.

Methods described herein are useful in multi-analyte assays (DNA, RNA, protein, etc.) from the same single cell.

Also described herein are compositions comprising cells and/or cell nuclei, a nuclear permeability enhancer, and a transposase or transposome complex.

BRIEF DESCRIPTION OF THE FIGURES

FIG. 2A shows access to cytoplasmic components of the cell alone by blocking the nuclear pores. FIG. 2B shows access to the nucleus by enhancing the permeability of the cell membrane, using cell permeable biomolecules, and/or enhancing the permeability of the nuclear membrane. FIG. 2C shows an isolated nucleus maintained individually as a contiguity element by use of a nuclear permeability enhancer.

FIG. 4A shows the ATAC-seq profile over a portion of Chr 12. FIG. 4B reports the diversity and uniqueness results for whole genome sequencing coverage. FIG. 4C shows normalized coverage over promoter and coding regions of the human genome.

FIG. 7A reports the concentration of ATAC-seq libraries based on BioAnalyzer data. FIG. 7B shows the ATAC-seq profile for two libraries over a portion of Chr 6.

FIG. 8A is a schematic representation of a bead-bound seeding oligonucleotide with a region complementary to an indexed PCR primer. FIG. 8B reports amplification efficiency obtained using the seeding oligonucleotide approach.

FIG. 9 shows agarose gel data for experiments with Bst and Phi29 strand-displacing polymerases as described in Example 13.

FIG. 11 shows single-cell sequencing data for mouse (3T3) ATAC-seq libraries prepared with 0 μM, 30 μM, and 60 μM Pitstop-2 added during cell lysis and transposition of nuclei. FIG. 11B shows the percentage of fragments for ATAC seq samples with 0 μM, 30 μM, or 60 μM Pitstop-2 within 1 kb of transcription start sites.

DETAILED DESCRIPTION

Figure 1:
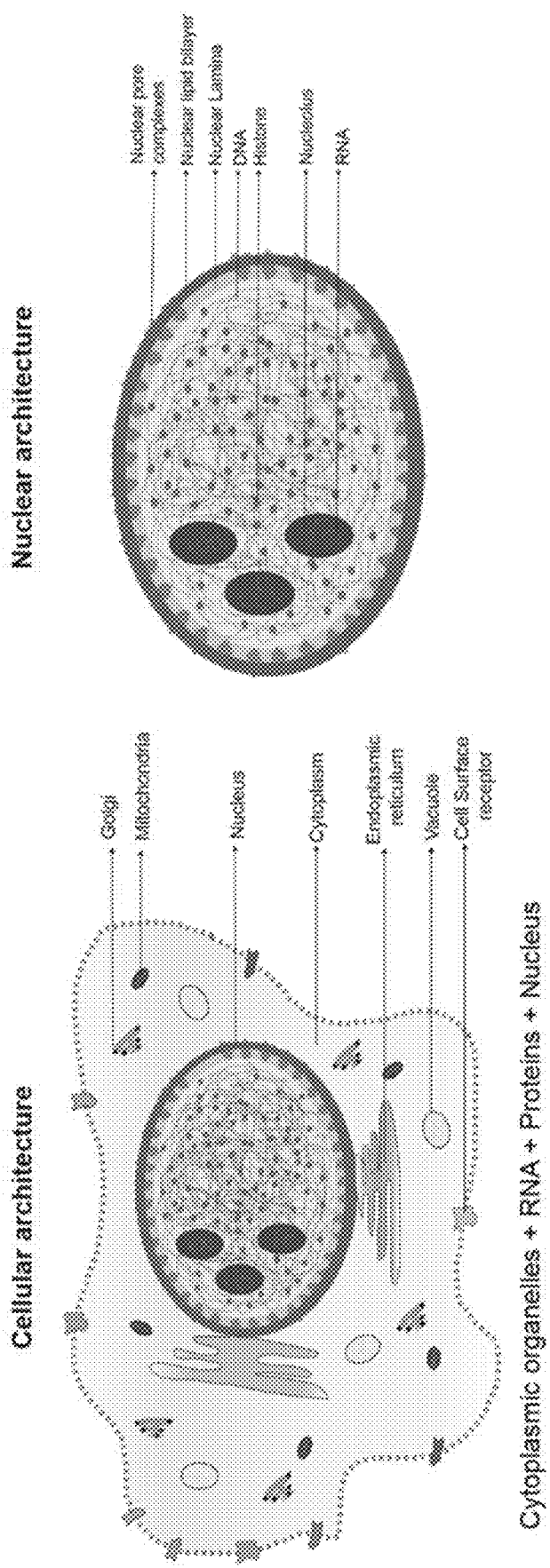
FIGS. 1A and 1B show the architecture of a cell (FIG. 1A) and a nucleus (FIG. 1B). The cytoplasm is confluent of proteins, RNA, mitochondrial DNA, and other biomolecules. The nucleus of the cell is confluent of DNA. RNA, nuclear proteins, and other biomolecules.

In some embodiments, a cell nucleus informational molecule is DNA, RNA, or protein. In some embodiments, it is DNA or mRNA. In some aspects, it is DNA. In some embodiments, it is RNA. In some embodiments, it is DNA and RNA. In some embodiments it is cDNA or cDNA and DNA. In some embodiments, the DNA can represent the open chromatin state of DNA. In some embodiments, the DNA can present whole genome DNA or a fraction of whole genome DNA or mitochondrial DNA.

In some embodiments, the cytoplasmic informational molecule is mRNA, DNA, or protein. In some embodiments, it is mRNA or DNA.

In some embodiments, an analytical biomolecule is a transposase or transposome complex, or an antibody, or an oligonucleotide, or a nucleotide, or a reverse transcription primer, or an enzyme. In some examples, the oligonucleotide or nucleotide comprises at least one labeled nucleotide. In some examples, the enzyme is an amplification enzyme, a polymerase, a DNA polymerase, a ligase, an RNA polymerase, a PCR enzyme, a Taq DNA polymerase, a Pfu DNA polymerase, an enzyme that mediates in vitro transcription, an integrase, or a nicking enzyme.

In some embodiments, the analytical biomolecule is indexed or barcoded. In some embodiments, the analytical biomolecule is a transposase. In other embodiments, it is a transposome complex. In some embodiments, the transposome complex comprises a transposase and two transposon end compositions comprising transposon end sequences. Suitable transposition methods are known in the art, and are described, for example, in U.S. Publ. Nos. 2010/0120098 and 2014/0194324, and PCT Publ. No. WO2016/130704.

In some embodiments, the transposon end compositions comprise end sequences and oligonucleotide adapters. In some embodiments, the particular transposon end sequences comprise a double-stranded region that binds to a recognition site of the transposase.

In some embodiments, the analytical biomolecule is an antibody, particularly, an antibody that binds specifically to a target informational molecule that is a protein, protein fragment, or peptide. Optionally, the antibody also comprises a pendant oligonucleotide or other tag that allows for subsequent isolation and/or analysis. Binding of the antibody to a target protein produces an analysis complex.

An "analysis complex" is the product of reaction of an analytical biomolecule and a target informational molecule. Such complexes may form through covalent or non-covalent binding, or both covalent and non-covalent binding. For example, a transposase complex may fragment and tag a target nucleic acid with a transferred strand, yielding a complex of the tagged nucleic acid, the transposase, and a non-transferred strand. The resulting analysis complex is formed through covalent bond and hybridization. In another example, an analysis complex may be an antibody-target protein or antibody-target peptide complex.

Methods and compositions are described to improve accessibility of transposomes to DNA into the nucleus. The current applications is not limited to transposomes as various other molecules can be selectively inserted into the nucleus or removed. For example, poly T capture probes can be brought into the nuclei for RNA capture and downstream assays (e.g., sequencing) and analysis. Alternatively, other pores like NPC can be targeted for transporting molecules in and out of the nuclei.

Examples of cytoplasmic and nuclear compartments are but not limited to mitochondria, nuclei, chloroplasts, peroxisomes, endoplasmic reticulum, microtubules, Golgi apparatus, carboxysomes, and metabolosomes.

Nuclear Permeability Enhancer

In some aspects, a nuclear permeability enhancer is a compound (e.g., a small molecule or peptide) that increases the permeability of the nuclear envelope without disrupting the nuclear membrane. In such embodiments, the nuclear membrane is not removed but becomes more porous. Such treatment improves access of analytical biomolecules, such as transposome complexes or antibodies, to nuclear genetic material. Thus, in some embodiments, access of the analytical biomolecule such as a transposome complex to nuclear genetic material is increased by contacting nuclei with a nuclear permeability enhancer. Suitable enhancers include compounds that disrupt NPC hydrophobic interactions, compounds that bind to and/or inhibit nuclear filament proteins such as clathrin, and nuclear localization signal peptides.

In some embodiments, the enhancer is a clathrin inhibitor. Inhibitors of clathrin coat assembly have been shown to inhibit uptake of classical substrates of clathrin-mediated endocytosis. (See Liashkovich, I. et al., "Clathrin inhibitor Pitstop-2 disrupts the nuclear pore complex permeability barrier," *Sci. Rep.* 2015, 5, 9994.) Such compounds may function to create cavities through and/or increase the size of nuclear pore complexes. Suitable clathrin inhibitors include Pitstop-2 (also known as N-[5-(4-bromobenzylidene)-4-oxo-4,5-dihydro-1,3-thiazol-2-yl]naphthalene-1-sulfonamide), methyl-β-cyclodextrin, phenothiazines, monodansylcadaverine, chloroquine, monensin, hyperosmotic sucrose, and dynasore, and synthetic analogs thereof. (See Chen, C.-L. et al., "Inhibitors of clathrin-dependent endocytosis enhance TGFβ signaling and responses," *J. Cell. Sci.* 2009, 122, 1863-1871, and references cited therein). As shown in the data presented herein, a clathrin inhibitor has been found to effect transport of transposome complexes into the nuclei, thereby improving access of transposome complexes to nuclear genetic material and improving transposition efficiency for that material.

Exemplary enhancers also include hydrophobicity disrupters such as aliphatic alcohols, including $C_{4-10}$-alkyl-diols, cyclic diols, cycloalkane-diols, or vicinal diols (e.g., trans-1,2-cyclohexanediol, n-hexane-1,2-diol, 1,6-hexanediol; see Ribbeck, K. et al., "The permeability barrier of nuclear pore complexes appears to operate via hydrophobic exclusion," *The EMBO J.* 2002, 21(11), 2664-2671). In some embodiments, the nuclear permeability enhancer is cyclohexanediol, or is 1,2-cyclohexanediol, or is trans-1,2-cyclohexanediol. Further hydrophobicity disrupters include surfactants such as digitonin (see, e.g., Hagstrom et al., *J. Cell Sci.* 1997, 110, 2323-2331; Tissera et al., "Nuclear envelopes show cell-type specific sensitivity for permeabilization with digitonin," *Nature* (Protocol Exchange), 2010 (available at https://www.nature.com/protocol exchange/protocol s/1994).

Exemplary enhancers also include nuclear localization signals (NLS), which are amino acid sequences typically used to tag proteins for import into the cell nucleus by nuclear transport. In some embodiments, the NLS is covalently or non-covalently linked to an analytical biomolecule (e.g., applied as a complex, or formed as a complex in situ). In some methods, the NLS is not covalently bound to an analytical biomolecule (e.g., transposase or transposome complex) but is used as an additive to the mixture of analytical biomolecule and cell or cell nucleus (e.g., transposition reaction). In some embodiments, the NLS is the SV40 Large T-antigen (PKKKRKV (SEQ ID NO: 1); Creative Peptides, Shirley, NY, Cat #GR1405), the NLS of nucleoplasmin (KR[PAATKKAGQA]KKKK (SEQ ID NO: 2) or AVKRPAATKKAGQAKKKLD (SEQ ID NO: 3)) (see Rotello et al., *Bioconj. Chem.* 26 (6), 1004-7), K-K/R-X-K/R (see Chelsky et al., *Mol. Cell Biol.* 1989, 9 (6), 2487-2492; Dingwall et al., *J. Cell. Biol.* 1988, 107 (3), 841), EGL-13 (MSRRRKANPTKLSENAKKLAKEVEN (SEQ ID NO: 4)), c-Myc (PAAKRVKLD (SEQ ID NO: 5)), TUS-protein (KLKIKRPVK (SEQ ID NO: 6)), the acidic M9 domain of hnRNP A1, KIPIK (SEQ ID NO: 7) from the yeast transcription repressor Mata2, PY-NLS sequences (Lee et al., *Cell* 126 (3), 543-58), and inhibitors of importin β2. In some embodiments, the NLS is the SV40 Large T-antigen.

Preparation of Template Nucleic Acids

Some embodiments include methods of preparing template nucleic acids. As used herein, "template nucleic acid" can refer to a substrate for obtaining sequence information. Some methods of preparing template nucleic acids include inserting a transposon sequence into a target nucleic acid, thereby preparing a template nucleic acid. Some methods of insertion include contacting a transposon sequence provided herein with a target nucleic acid in the presence of an enzyme, such as a transposase or integrase, under conditions sufficient for the integration of the transposon sequence or sequences into the target nucleic acid. In some embodiments, a template nucleic acid can include a target nucleic acid, a fragment thereof, or any copy thereof comprising at least one transposon sequence, a fragment thereof, or any copy thereof. In some embodiments, a template nucleic acid can include a target nucleic acid comprising an adaptor comprising a tag suitable for sequencing, such as a primer site.

In some embodiments, the cells can be fixed. In some embodiments, the methods described herein employ intact cells, and fix cells by treatment with a surfactant. In such methods, analytical biomolecules can enter the cells without disruption of the cell membrane. In exemplary methods, cells are treated with a surfactant (e.g., NP-40, SDS, etc.), a nuclear permeability enhancer, and an analytical biomolecule.

In some embodiments, analytical biomolecules are designed for particular target DNA, mRNA, cDNA, DNA, or any combination thereof (e.g., DNA and cDNA). For example, certain analytical biomolecules may include index probes designed to distinguish between DNA and mRNA. In some embodiments, a first analytical molecule and a second analytical biomolecule are used, e.g., a first transposome complex and a second transposome complex, where the first transposome complex comprises a transposon end sequence for tagging DNA (e.g., A14/B15 primer sequences) and the second transposome complex comprises a transposon end sequence for tagging mRNA (e.g., comprising an adaptor comprising a polyT region that is specific for the mRNA poly A tail).

In some embodiments, artificial pores can be inserted into cellular or nuclear compartments to facilitate transfer of analytical biomolecules in or out of the compartment.

In some embodiments, methods include isolating cell nuclei. Isolation of cell nuclei may be accomplished using standard methods known in the art, provided that the methods retain the integrity of the cell nuclei. In some instances, cell lysis methods may be used. Cell nuclei may be isolated or purified away from cytoplasmic components prior to exposure to the nuclear permeability enhancer. In some embodiments, the cytoplasmic fraction is maintained and analyzed separately.

For nucleic acid analysis, sample preparation typically involves fragmenting genomic nucleic acids into sequenceable lengths, and ligating adaptors to the fragments to yield templates for subsequent purification and, if needed, amplification. Templates are converted using primers into "seeding" templates, which are amplified and subjected to sequencing protocols.

The number of steps required to transform DNA and/or RNA into adaptor-modified templates in solution ready for amplification and sequencing can be minimized by the use of transposase-mediated fragmentation and tagging. This process, referred to herein as "tagmentation," often involves the modification of DNA or mRNA by a transposome complex comprising transposase enzyme complexed with adaptors comprising transposon end sequence. Tagmentation results in the simultaneous fragmentation of the DNA and ligation of adaptors to the 5' ends of both strands of duplex fragments. A purification step can be used to remove the transposase enzyme. Any gaps in the double-stranded product may be filled, and additional sequences can be added to the ends of the adapted fragments by PCR.

In some embodiments, a plurality of the transposon sequences provided herein is inserted into a target nucleic acid. Some embodiments include selecting conditions sufficient to achieve integration of a plurality of transposon sequences into a target nucleic acid such that the average distance between each integrated transposon sequence comprises a certain number of consecutive nucleotides in the target nucleic acid.

Some embodiments of preparing a template nucleic acid can include copying the sequences comprising the target nucleic acid. For example, some embodiments include hybridizing a primer to a primer site of a transposon sequence integrated into the target nucleic acid. In some such embodiments, the primer can be hybridized to the primer site and extended. The copied sequences can include at least one barcode sequence and at least a portion of the target nucleic acid. In some embodiments, the copied sequences can include a first barcode sequence, a second barcode sequence, and at least a portion of a target nucleic acid disposed therebetween. In some embodiments, at least one copied nucleic acid can include at least a first barcode sequence of a first copied nucleic acid that can be identified or designated to be paired with a second barcode sequence of a second copied nucleic acid. In some embodiments, the primer can include a sequencing primer. In some embodiments sequencing data is obtained using the sequencing primer. In more embodiments, adaptors comprising primer sites can be ligated to each end of a nucleic acid, and the nucleic amplified from such primer sites.

Some embodiments of preparing a template nucleic acid can include amplifying sequences comprising at least a portion of one or more transposon sequences and at least a portion of a target nucleic acid. In some embodiments, at least a portion of a target nucleic acid can be amplified using primers that hybridize to primer sites of integrated transposon sequences integrated into a target nucleic acid. In some such embodiments, an amplified nucleic acid can include a first barcode sequence, and second barcode sequence having at least a portion of the target nucleic acid disposed therebetween. In some embodiments, at least one amplified nucleic acid can include at least a first barcode sequence of a first amplified nucleic acid that can be identified to be paired with a second barcode sequence of a second amplified sequence.

In some embodiments, it can be advantageous for each template nucleic acid to incorporate at least one universal primer site. For example, a template nucleic acid can include first end sequences that comprise a first universal primer site, and second end sequences that comprise a second universal primer site. Universal primer sites can have various applications, such as use in amplifying, sequencing, and/or identifying one or more template nucleic acids. The first and second universal primer sites can be the same, substantially similar, similar, or different. Universal primer sites can be introduced into nucleic acids by various methods well known in the art, for example, ligation of primer sites to nucleic acids, amplification of nucleic acids using tailed primers, and insertion of a transposon sequence comprising a universal primer site.

Transposomes

As used herein, the term "transposome complex" refers generally to a transposition enzyme (e.g., an integrase or transposase) and a double-stranded nucleic acid comprising an integration recognition site, such as a transposase recognition site. In embodiments provided herein, a transposase can form a functional complex with a transposase recognition site that is capable of catalyzing a transposition reaction. The transposase may bind to the transposase recognition site and insert the transposase recognition site into a target nucleic acid via "tagmentation." In some such insertion events, one strand of the transposase recognition site may be transferred into the target nucleic acid. In one example, a transposome comprises a dimeric transposase comprising two subunits, and two non-contiguous transposon sequences. In another example, a transposase comprises a dimeric transposase comprising two subunits, and a contiguous transposon sequence. In some embodiments, a complex is formed by incubating a transposase with double-stranded transposon DNA under conditions that support non-covalent complex formation.

Double-stranded transposon DNA can include, without limitation, Tn5 DNA, a portion of Tn5 DNA, a transposon end composition, a mixture of transposon end compositions, or other double-stranded DNAs capable of interacting with a transposase such as the hyperactive Tn5 transposase.

A "transposase" means an enzyme that is capable of forming a functional complex with a transposon end-containing composition (e.g., transposons, transposon ends, transposon end compositions) and catalyzing insertion or transposition of the transposon end-containing composition into the double-stranded target DNA with which it is incubated, for example, in an in vitro transposition reaction. A transposase as presented herein can also include integrases from retrotransposons and retroviruses.

Transposases, transposomes, and transposome complexes are generally known to those of skill in the art, as exemplified by the disclosure of U.S. Publ. No. 2010/0120098 and PCT Publ. No. 2016/130704, which are incorporated herein by reference. Transposase enzymes include, but are not limited to, Tn5 transposase, a Mu transposase, and *Vibrio harveyi* transposase, and variants thereof, such as hyperactive Tn5 transposase. Transposase enzymes may be multimers, such as dimers, trimers, or tetramers, such as a Tn5 dimer. Any transposition system that is capable of inserting a transposon end with sufficient efficiency to tag and fragment a target DNA for its intended purpose can be used in the methods described herein. In particular embodiments, a preferred transposition system is capable of inserting the transposon end in a random or in an almost random manner to 5'-tag and fragment the target DNA. In particular embodiments are hyperactive Tn5 transposase and a Tn5-type transposase recognition site (Goryshin and Reznikoff, *J. Biol. Chem.* 1983, 273:7367), or MuA transposase and a Mu transposase recognition site comprising R1 and R2 end sequences (Mizuuchi, K., *Cell* 1983, 35:785; Savilahti, H. et al., *EMBO J.* 1995, 14:4893). Mosaic end (ME) sequences can also be used as optimized by a skilled artisan. The above references are incorporated herein by reference. Further exemplary transposition systems are described in WO2016/130704, such as *S. aureus* Tn552, Ty1, Transposon Tn7, Tn/O and IS10, Mariner transposase, Tc1, P Element, Tn3, bacterial insertion sequences, retroviruses, retroviral integrases (such as integrases from HIV-1, HIV-2, SIV, PFV-1, and RSV), retrotransposon of yeast, IS5, Tn10, Tn903, or IS911, and engineered variants thereof.

In some embodiments, the transposase is a Tn5 transposase, a Mu transposase, or a *Vibrio* (e.g., *Vibrio harveyi*) transposase. In some embodiments, the transposase is a Tn5 transposase. In some embodiments, the transposase is a hyperactive Tn5 transposase. In some embodiments, the transposase is a dimer. In some embodiments, the transposase is a Tn5 dimer. In some embodiments, the Tn5 dimer is hyperactive.

Transposon Sequences

The term "transposon end" refers to a double-stranded nucleic acid DNA includes at least one transposition recognition site (the "transposon end sequences") that form a complex with the transposase or integrase enzyme to provide a transposome complex for in an in vitro transposition reaction. Transposon sequences useful with the methods and compositions provided herein are provided in U.S. Publ. Nos. 2012/0208705 and 2012/0208724, and PCT Publ. No. WO 2012/061832, each of which is incorporated by reference in its entirety. In some embodiments, a transposon end is capable of forming a functional complex with the transposase in a transposition reaction. As non-limiting examples, transposon ends can include the 19-bp outer end ("OE") transposon end, inner end ("IE") transposon end, or "mosaic end" ("ME") transposon end recognized by a wild-type or mutant Tn5 transposase, or the R1 and R2 transposon end as described in U.S. Publ. No. 2010/0120098. Transposon ends can comprise any nucleic acid or nucleic acid analog suitable for forming a functional complex with the transposase or integrase enzyme in an in vitro transposition reaction. For example, the transposon end can comprise DNA, RNA, modified bases, non-natural bases, and/or a modified backbone, and can comprise nicks in one or both strands. Although the term "DNA" is used throughout the present disclosure in connection with the composition of transposon ends, it should be understood that any suitable nucleic acid or nucleic acid analogue can be utilized in a transposon end.

The term "transferred strand" refers to the transferred portion of both transposon ends. Similarly, the term "non-transferred strand" refers to the non-transferred portion of both "transposon ends." The 3'-end of a transferred strand is joined or transferred to target DNA in an in vitro transposition reaction. The non-transferred strand, which exhibits a transposon end sequence that is complementary to the transferred transposon end sequence, is not joined or transferred to the target DNA in an in vitro transposition reaction.

The term "adaptor" as used herein refers to a polynucleotide region comprising at least one tag. Some embodiments include a transposome complex comprising a polynucleotide having a 3' portion comprising a transposon end sequence, and an adaptor region comprising at least one tag. Adaptor sequences may include linker regions.

The term "tag" as used herein refers to an oligonucleotide region with a sequence suitable for a desired intended purpose or application. A tag may comprise one or more sequences that are useful when inserted into a target nucleic acid, such as fragmentation sites (sequence that may be cleaved chemically, biochemically, or photochemically at a determined time), primer sites, barcodes (used to identify one or more particular analytes), affinity tags, recognition sites, and/or reporter moieties (moiety that can emit a signal, e.g., fluorescent, chemiluminescent, bioluminescent, phosphorescent, radioactive, calorimetric, electronic, or other signal). It will be appreciated that any other suitable feature can be incorporated into a tag. In some embodiments, the tag comprises a sequence having a length between 5 and 200 bp, or between 10 and 100 bp, or between 20 and 50 bp, or having a length of about 5, 6, 7, 8, 9, 10, 20, 30, 40, 50, 60, 70, 80, 90, 100, 150, or 200 bp.

In some embodiments, a tag comprises one or more primer sites suitable for hybridization with a primer (which may be bound to a solid surface such as a bead or flow cell) for an amplification reaction such as cluster amplification and/or a sequencing reaction. Exemplary sequences of primer binding sites include, but are not limited to:

```
(P5 sequence)
                                    (SEQ ID NO: 8)
AATGATACGGCGACCACCGAGATCTACAC
and (P7 sequence)
                                    (SEQ ID NO: 9)
CAAGCAGAAGACGGCATACGAGAT
``` and complements thereof. In some instances, the primer sequence include modified bases to allow for subsequent enzymatic or chemical cleavage, such as a vicinal diol or an 8-oxo-guanine. In some embodiments, tags comprise barcodes that are used in the preparation of template nucleic acids. As will be understood, the vast number of available barcodes permits each template nucleic acid molecule to comprise a unique identification. Unique identification of each molecule in a mixture of template nucleic acids can be used in several applications. For example, uniquely identified molecules can be applied to identify individual nucleic acid molecules, in samples having multiple chromosomes, in genomes, in cells, in cell types, in cell disease states, and in species, for example, in haplotype sequencing, in parental allele discrimination, in metagenomic sequencing, and in sample sequencing of a genome. Exemplary barcode sequences include, but are not limited to TATAGCCT, ATAGAGGC, CCTATCCT, GGCTCTGA, AGGCGAAG, TAATCTTA, CAGGACGT, and GTACTGAC.

Methods for preparing transposon end sequences, transposons, and transposome complexes are known in the art.

As used herein, the terms "nucleic acid" and "oligonucleotide" refer to at least two nucleotide monomers covalently linked together. A nucleic acid generally contains phosphodiester bonds and natural bases, but in some embodiments may comprise non-natural backbones and/or bases, as described, for example, in PCT Publ. No. WO2016/130704. The nucleic acid may be DNA, for example, genomic or cDNA, RNA or a hybrid, from single cells, single nuclei, multiple cells, multiple nuclei, or from multiple species, as with metagenomic samples, such as from environmental samples, further from mixed samples for example mixed tissue samples or mixed samples for different individuals of the same species, disease samples such as cancer related nucleic acids, and the like. A nucleic acid can contain any combination of deoxyribo- and ribo-nucleotides, and any combination of bases, including natural bases, or non-natural, analog, or synthetic bases.

As used herein, the term "detect" and/or grammatical equivalents thereof can refer to identifying the presence or existence of an analyte, identifying the individual components of an analyte, for example, sequence information, and/or quantifying the amount of such analyte. In some embodiments, detecting comprises detecting the sequences of tagged informational molecules or amplicons produced by the methods described herein.

In some embodiments, target informational molecules, cells, and/or nuclei may be obtained from any biological specimen comprising DNA and/or mRNA, including but not limited to a biological sample or a patient sample. The source of the cells and/or cell nuclei may be, for example, bacteria, plants, parasites, insects, animals, or mammals (e.g., rat, mouse, monkey, non-human primate, human), or a mixture thereof. The term "biological sample" or "patient sample" as used herein includes samples such as one or more cells, tissues, or bodily fluids. Samples may include natural or processed samples, such as macerated tissue or lysates. "Bodily fluids" may include, but are not limited to, blood, serum, plasma, saliva, cerebrospinal fluid, bronchial aspirate, pleural fluid, bursa fluid, synovial fluid, tears, lactal duct fluid, lymph, mucus, sputum, urine, feces, amniotic fluid, or semen, or mixtures thereof. Tissues may include biopsy samples, tumor samples, or skin. A sample may include a bodily fluid that includes less than about 1% (w/w) whole cellular material, such as plasma or serum. A sample may include a specimen of natural or synthetic origin (i.e., a cellular sample made to be acellular).

In some embodiments, the methods further comprise treating the tagmented nucleic acid with a polymerase such as a strand-displacing polymerase (e.g., Bst polymerase or Phi29 polymerase) to remove the transposase from the tagmented material. In such embodiments, tagmented nucleic acids within nuclei may be treated with a polymerase (e.g., a strand-displacing polymerase) and sodium dodecyl sulfate to allow for PCR amplification. In other embodiments, tagged informational molecules may be treated with a polymerase, such as a strand-displacing polymerase, to allow for PCR amplification.

In some embodiments, methods further comprise contacting transposed cell nuclei with deionized water. Thus, methods may further comprise removing analytical complexes, such as tagged nucleic acids or antibody-protein/peptide complexes from treated cells or nuclei by treating the cells or nuclei with deionized water. Such treatment creates an osmotic influx of water thereby swelling the nuclear body. In some embodiments, treatment of cells or nuclei with a nuclear permeability enhancer includes treatment with deionized water. Such swelling serves to further increase the nuclear pore size to allow further influx of transposome complexes into the nuclear space. (See FIG. 10.)

In some embodiments, treatment with a nuclear permeability enhancer occurs in the presence of a high-salt buffer. The buffer generates an osmotic differential across the nuclear membrane so that nuclear material is expelled out of the nuclear body. Such treatment would allow for temporal control over disruption of the nuclear membrane. (See FIG. 10.)

Without treatment of nuclei with a permeability enhancer, small amounts of transposome complexes do gain access to nuclear material. Thus, in some embodiments, methods comprise reacting a cytoplasmic informational molecule with a first analytical biomolecule in the presence of a nuclear pore blocker and in the absence of a nuclear permeability enhancer. In a subsequent step, the nuclear pore blocker and/or cytoplasmic material is optionally removed, and the remaining cellular material is treated with a second analytical biomolecule in the presence of a nuclear permeability enhancer. In this way, the cytoplasmic and nuclear components are orthogonally tagged. Suitable nuclear pore blockers include agents such as wheat germ agglutinin, leptomycin B, antibodies specific to the NPC (see, e.g., Adam, S. A. et al., *J. Cell Biol.* 1990, 111(3), 807-816; Moore et al., Cell 1992, 69(6), 939-950), or other ligands, enzymes, or biomolecules that bind to NPCs or gated ion channels.

Contiguity Preserving Elements

In some embodiments, contiguity preserving elements (CEs) are employed to preserve single cell and/or single nucleus information. In some embodiments, contiguity information of single nuclei is preserved by compartmentalization of individual nuclei or individual cells. In some embodiments, such compartmentalization is accomplished by localizing single nuclei or cells in physical compartments such as microwells, microdroplets, or microcapsules, or by immobilizing genetic material using hydrogels or on or within microbeads. Such processes effectively maintain the cellular and/or nuclear contiguity during transposition while giving more direct access to the nuclear material. Such approaches also reduce cross contamination of nuclear material from separate nuclei. In some embodiments, a CE may comprise a target nucleic acid.

In some embodiments, the methods include sequencing nucleic acids preserved, embedded, or contained within contiguity preserving elements. In particular, embodiments of the methods and compositions provided herein relate to preparing nucleic acid templates and obtaining sequence data therefrom. Methods and compositions provided herein are related to the methods and compositions provided in U.S. Publ. Nos. 2012/0208705 and 2012/0208724 and PCT Publ. No. WO 2012/061832, each of which is incorporated by reference in its entirety. Some embodiments presented herein relate to preparing DNA within contiguity preserving element(s) to obtain phasing and sequence assembly information from a target nucleic acid, and obtaining phasing and sequence assembly sequence information from such templates. Particular embodiments provided herein relate to the use of integrases, for example transposases, to maintain physical proximity of associated ends of fragmented nucleic acids; and to the use of combinatorial indexing to create individual libraries from each contiguity preserving element. Obtaining haplotype information includes distinguishing between different alleles (e.g., SNPs, genetic anomalies, etc.) in a target nucleic acid. Such methods are useful to characterize different alleles in a target nucleic acid, and to reduce the error rate in sequence information.

In some embodiments, the CE comprises cells or a single cell. In some embodiments, the CE comprises nucleic acids from cells or from a single cell, such as DNA, mRNA, or cDNA; macromolecules of cells or of a single cell including proteins, polysaccharides, lipids, and nucleic acids, as well as small molecules such as primary metabolites, secondary metabolites, and natural products from cells or from a single cell. In some embodiments, the nucleic acid undergoes amplification such as, PCR or whole genome amplification before forming the CE comprising the nucleic acid. In some embodiments, analysis of the DNA and mRNA can be performed in parallel. In some embodiments, the cell membrane is a CE.

In some embodiments, the CE comprises nuclei or a single nucleus. In some embodiments, the CE comprises nucleic acid from nuclei or from a single nucleus. In some embodiments, the nuclear membrane is a CE.

Figure 2:
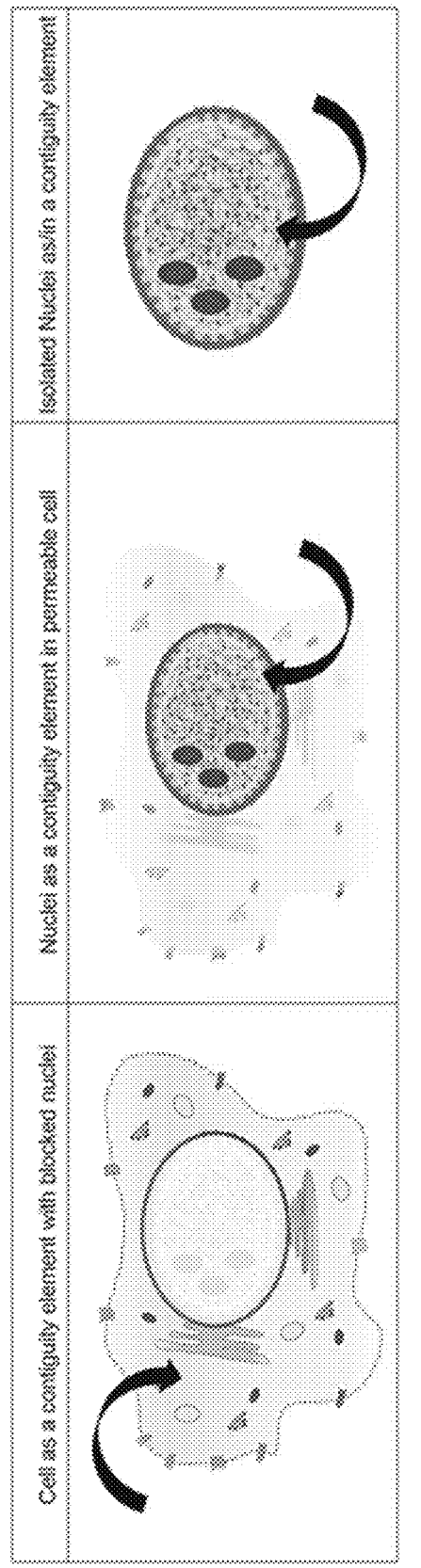
FIGS. 2A, 2B, and 2C show different modes of access to cellular and nuclear components.

As shown in FIG. 2, the present disclosure contemplates various modes of access to cellular and nuclear compartments that maintain contiguity information. In some embodiments, the cell is a CE element in which the nucleus (e.g., nuclear pore complexes) is blocked to entry of analytical biomolecules or reagents needed to allow interaction of nuclear informational molecules with analytical biomolecules (FIG. 2A). The nuclear membrane is therefore a CE that allows for differential reaction with cytoplasmic versus nuclear content. In such instances, the cell membrane may be used as a second CE, or the cell may be compartmentalized in a further CE. In some embodiments, nuclear content is accessed by enhancing the permeability of the cell membrane, using cell permeable biomolecules, and/or enhancing the permeability of the nuclear membrane (FIG. 2B). In other embodiments, the nuclear membrane of isolated nuclei can serve as a CE (FIG. 2C) when treated with a nuclear permeability enhancer. All of these methods can be used in conjunction with additional CEs, such as microdroplets, microbeads (hydrogels), microwells, and other kinds of compartments, to maintain information contiguity.

In some embodiments are methods of preparing libraries from RNA, DNA, or mixtures thereof, and obtaining single cell data for RNA, DNA, or both RNA and DNA. In some embodiments are methods of preparing libraries from RNA, DNA, proteins, or any combination thereof.

In some embodiments, cells are lysed within the CE such that the plurality of target informational molecules within the single cell are released within the CE. In some instances, the cell is lysed but the nucleus is not lysed, such that cytoplasmic components are released within the CE and nuclei remain intact.

In some embodiments, multiple CEs are employed in conjunction with a combinatorial tagging approach, so that nucleic acids or other informational molecules are physically partitioned and/or orthogonally tagged.

In one embodiment, targets can be diluted into CE such as droplets. Optional whole genome amplification may be employed, and sequence information can be obtained from an amount of template nucleic acid equivalent to about a haploid equivalent of the target nucleic acid.

In some embodiments, multiple combinatorial labeling scheme may be employed to the components within a single cell in addition to the nucleic acid, for example, proteins, organelles, lipids, or cell membranes such that the components within a single cell or nucleus can be identified from the components from a different single cell or nucleus. In some embodiments, a CE may comprise the components within a single cell or a single nucleus. In some embodiments, the components of a single cell and/or single nucleus within a CE will have identifiable unique label(s) that are different from the components of a single cell and/or nucleus within a different CE.

In some embodiments, multiple combinatorial barcoding schemes may be employed. In some embodiments, such combinatorial barcoding and combinatorial labeling may be performed within a CE comprising a single cell. In some embodiments, such combinatorial barcoding and combinatorial labeling may be performed for multiple CE comprising single cells or nuclei in parallel.

A contiguity preserving element (CE) is a physical entity which preserves at least two, or more, or all analytes in close proximity (or contiguity) through one or more assay steps and provides access to assay reagents and can be pooled and split multiple times without losing the proximity of the analytes.

In some embodiments, the CE can be a solid support. In one embodiment, the CE may be an emulsion or droplet. In some embodiments, the CE is gel, hydrogel, or gel bead. In some embodiments, the CE may comprise a solid support such as beads. In some embodiments, the beads may further comprise antibodies, oligonucleotides, and/or barcodes. In another embodiment, the CE may constitute a DNA nanoball created by WGA, RCA, or condensation of any nucleic acid reagent.

In some embodiments, a CE can be made by embedding the nucleic acid from cells or from a single cell, or the amplification product thereof (from WGA, etc.) in a polymer matrix such as agarose, polyacrylamide, alginate, etc. In some embodiments, the contiguity of the contents of the cells or of a single cell within a CE are maintained by preserving physical proximity of the components to one another through encapsulation (such as in a polymer matrix), immobilization on a bead or entrapment, effectively maintaining contiguity information within the CE through repeated rounds of pooling and redistribution. The feature that a collection of CE can be independently pooled and split, reacted with assay reagents, pooled and split again, etc. yet maintaining the contiguity of the analytes constituting an individual CE enables the combinatorial indexing through different split and pool steps.

In some embodiments, the analytes in the contiguity preserving element are accessible to assay reagents including aqueous solutions, enzymes (e.g., fragmentases, polymerases, ligases, transposases, kinases, restriction endonucleases, proteases, phosphatases, or lipases), nucleic acid adapters, nucleic acid barcodes, and/or labels.

In some embodiments, one or more analytes of a CE is labeled with one or more labels. Exemplary labels include but are not limited to DNA barcodes or indices, fluorescent labels, chemiluminescent labels, RNA barcodes or indices, radioactive labels, antibody comprising a label, beads comprising a label.

In some embodiments, a method can include the steps of: (a) compartmentalizing the CE comprising target nucleic acid into a plurality of first vessels; (b) providing a first index to the target nucleic acid of each first vessel, thereby obtaining a first indexed nucleic acid; (c) combining the first indexed nucleic acids; (d) compartmentalizing the first indexed template nucleic acids into a plurality of second vessels; (e) providing a second index to the first indexed template nucleic acid of each second vessel, thereby obtaining a second indexed nucleic acid. The steps a-e can be continued with additional cycles of one or more steps from the a-e series to derive additional virtual compartments. This method of combinatorial indexing can be used to effectively create a large number of virtual compartments from a limited number of physical compartments.

In some embodiments, a method can include the steps of: (a) providing a CE comprising non-nucleic acid analytes (e.g. proteins) with attached nucleic acid reporters; (b) compartmentalizing the CE into a plurality of first vessels; (c) providing a first index to the target nucleic acid reporters of each first vessel, thereby obtaining a first indexed target nucleic acid reporter; (d) combining the first indexed nucleic acid reporters; (e) compartmentalizing the first indexed CEs into a plurality of second vessels; (f) providing a second index to the first indexed nucleic acid reporters of each second vessel, thereby obtaining a second indexed nucleic acid reporter. The steps a-f can be continued with additional cycles of one or more steps from the a-f series to derive additional virtual compartments. The compartmentalization step can further include nucleic acid amplification or capture step such as PLA, PEA, or other technique that captures or amplifies nucleic acids.

In some embodiments, a nucleic acid or nucleic acids can be embedded in a matrix that confines the nucleic acids to a defined space but allows reagent access to perform steps including, but not limited to, amplification (PCR, whole-genome amplification, random primer extension, etc.), ligation, transposition, hybridization, restriction digestion and DNA mutagenesis. Examples of mutagenesis include, but are not limited to, error-prone extension, alkylation, bisulfite conversion, and activation-induced (cytidine) deaminases, etc.

In some embodiments, an analyte of interest in a CE is a protein. Proteins can be labeled with barcodes or alternative labels. The barcode or labels can be read out using traditional arrays or sequence-based methods. Proximity ligation approaches and antibody-index sequences can be used to detect proteins (Fredriksson et al., *Nature Biotechnology* 20, 473-477 (2002), incorporated herein by reference) together with the detection of the barcode sequences to establish identity and abundance of the proteins in each individual cell. Proteins can be labeled by various methods (www.piercenet.com/cat/protein-antibody-labeling) known by a skilled worker including in vivo and in vitro site-specific chemical labeling strategies.

In some embodiments, contiguity preserving elements may comprise a single cell and the nucleic acid from the cell may be amplified. Subsequently, each contiguity preserving element can be uniquely indexed through the combinatorial indexing scheme. In some embodiments, a combinatorial indexing approach may be used. For example, initial indexes are attached to the genomic DNA or cDNA through standard library preparation techniques using fragmentation (enzymatic) and adapter ligation, or through tagmentation using transposase complexes. Subsequent indexes are attached to the library via ligation or PCR. Ligation is preferred since it is easy to add indexed adapters in a sequential fashion. The final step may involve just indexed PCR or ligation and PCR.

Differential indexing of cellular biomolecules: Cellular and sub-cellular compartments containing biomolecules such as DNA, RNA, mitochondrial DNA, proteins etc., can be specifically and orthogonally indexed for genomic assays by preserving cellular contiguity. This can be achieved by differential targeting of membrane proteins of sub-cellular compartments (cell membrane, nuclear membrane, and mitochondrial membrane) to allow for selective transport of ions or other proteins into certain compartments but not into others. For example, nuclear membrane proteins can be blocked with blocker molecules such as Wheat germ agglutinin, leptomycin B, and antibodies specific to NPC, while Cyclosporin A, Oligomycin, and other compounds block mitochondrial membrane proteins. This approach allows for indexing genetic material (not limited to transposition, spliced-ligation, etc.,) within sub-cellular compartments of the cell, giving better, refined sequencing reads targeted specifically within a cell.

In some aspects, described herein are methods of differentially indexing informational molecules from different compartments of a cell. In some aspects, such methods comprise:

selectively delivering a first analytical biomolecule comprising a first tag to a first cellular compartment selected from the group consisting of the cell nucleus, the cytoplasm, and the mitochondria, wherein the first cellular compartment comprises a first informational biomolecule;

reacting the first analytical biomolecule with the first informational molecule to provide a tagged first informational molecule;

selectively delivering a second analytical biomolecule comprising a second tag to a second cellular compartment selected from the group consisting of the cell nucleus, the cytoplasm, and the mitochondria, wherein the second cellular compartment comprises a second informational molecule and is different from the first cellular compartment; and reacting the second analytical biomolecule with the second informational molecule to provide a tagged second informational molecule, wherein the first and second tags are different.

In some embodiments is a method of differentially indexing cytoplasmic and nuclear informational molecules, comprising: (a) delivering a first analytical biomolecule comprising a first tag to the cytoplasm of a cell without substantial delivery of the first analytical biomolecule to the nucleus of the cell; (b) reacting the first analytical biomolecule with a cytoplasmic informational molecule, thereby adding the first tag or a complement thereof to the cytoplasmic informational molecule to provide a tagged cytoplasmic informational molecule; (c) treating the cell with a nuclear permeability enhancer and a second analytical biomolecule comprising a second tag, thereby delivering the second analytical biomolecule to the nucleus of the cell; and (d) reacting the second analytical biomolecule with a cell nucleus informational molecule, thereby adding the second tag or a complement thereof to the cell nucleus informational molecule to provide a tagged cell nucleus informational molecule. In some embodiments, the delivery to the cytoplasm further comprises treating the cell with a nuclear pore blocker and/or a mitochondrial pore blocker. In some embodiments, the method further comprises lysing the cells to release the tagged molecules. In some embodiments, the first and second tags are orthogonal such that they are distinguishable when detected, or may be targeted separately in subsequent manipulation steps such as amplification. In some embodiments, the cytoplasmic informational molecule is RNA. In some embodiments, the cell nucleus informational molecule is DNA or genomic DNA (gDNA). In some embodiments, the analytical biomolecules are transposomes. In some embodiments, the method further comprises detection of the tagged molecules or their amplicons. In some embodiments, the method further comprises selective amplification of the tagged molecules (e.g., first tagged over second tagged or the reverse).

In other aspects, the method comprises: (a) reacting a first analytical biomolecule comprising a first tag with a mitochondrial informational molecule to produce a tagged mitochondrial informational molecule; (b) reacting a second analytical biomolecule comprising a second tag with a cell nucleus informational molecule to produce a tagged cell nucleus informational molecule. In some embodiments, the method further comprises: delivering the first analytical biomolecule to the mitochondria by treating a cell with a mitochondrial membrane permeability enhancer and the first analytical biomolecule. In some embodiments, the delivery to the mitochondria further comprises treating the cell with a nuclear pore blocker. In some embodiments, the delivery to the mitochondria does not include substantial delivery of the first analytical biomolecule to the nucleus of the cell. In some aspects, the mitochondrial informational molecule is DNA. In some aspects, the cell nucleus informational molecule is DNA, or is genomic DNA (gDNA). In some embodiments, the first and second tags are orthogonal such that they are distinguishable when detected, or may be targeted separately in subsequent manipulation steps such as amplification. In some embodiments, the analytical biomolecules are transposomes. In some embodiments, the method further comprises detection of the tagged molecules or their amplicons.

In some aspects, the selective delivering of the first analytical biomolecule to the first cellular compartment comprises comprises treating the cell with a permeability enhancer for the first cellular compartment. In some embodiments, the selective delivering of the first analytical biomolecule to the first cellular compartment comprises treating the cell with a permeability blocker for the second cellular compartment. In some embodiments, the selective delivering of the second analytical biomolecule to the second cellular compartment comprises treating the cell with a permeability enhancer for the second cellular compartment. In some embodiments, the selective delivering of the first analytical biomolecule occurs without substantial delivery of the first analytical biomolecule to the second cellular compartment.

In some embodiments, the first cellular compartment is the cytoplasm and the first informational molecule is a cytoplasmic informational molecule, and (a) the second cellular compartment is the cell nucleus and the second informational molecule is a cell nucleus informational molecule or (b) the second cellular compartment is the mitochondria and the second informational molecule is a mitochondrial informational molecule. In some embodiments, the selective delivering of the first analytical biomolecule to the cytoplasm is done in the presence of a nuclear pore blocker and/or a mitochondrial pore blocker. In some embodiments, the delivery of the second analytical biomolecule is done in the presence of a nuclear permeability enhancer or a mitochondrial permeability enhancer.

As used herein, a "mitochondrial permeability enhancer" enhances permeability of a mitochondria to reagents such as enzymes. Such enhancers do not lyse the mitochondria. Exemplary mitochondrial permeability enhancers include agents that increase flow through mitochondrial pores. Examples include inorganic polyphosphate (see, e.g., Seidlmayer et al., J. Gen. Physiol. 2012, 139(5), 321-331).

As used herein, the term "selective delivering" or grammatical variations thereof refers to enhanced delivery of an agent to one cellular compartment over another. Selective delivery may be accomplished by enhancing permeability of one compartment or blocking permeability of one compartment relative to permeability of the compartments when untreated. Selective delivery does not need to be 100% selective, but can include increasing the relative fractions of tagged informational molecules from different compartments in the resulting library.

Analysis and Sequencing

Some of the methods provided herein include methods of analyzing nucleic acids. Such methods include preparing a library of template nucleic acids of a target nucleic acid, obtaining sequence data from the library of template nucleic acids, and assembling a sequence representation of the target nucleic acid from such sequence data.

Target nucleic acids and template nucleic acids can be enriched for certain sequences of interest using various methods well known in the art. Examples of such methods are provided in PCT Publ. No. WO2012/108864, which is incorporated herein by reference in its entirety. In some embodiments, nucleic acids may be further enriched during methods of preparing template libraries. For example, nucleic acids may be enriched for certain sequences, before tagmentation, after tagmentation, and/or after amplification of nucleic acids.

Some embodiments of the technology described herein include methods of analyzing template nucleic acids. In such embodiments, sequencing information can be obtained from template nucleic acids and this information can be used to generate a sequence representation of one or more target nucleic acids.

In some embodiments of the sequencing methods described herein, a linked read strategy may be used. A linked read strategy can include identifying sequencing data that links at least two sequencing reads. For example, a first sequencing read may contain a first marker, and a second sequencing read may contain a second marker. The first and second markers can identify the sequencing data from each sequencing read to be adjacent in a sequence representation of the target nucleic acid. In some embodiments of the compositions and methods described herein, markers can comprise a first barcode sequence and a second barcode sequence in which the first barcode sequence can be paired with the second barcode sequence. In other embodiments, markers can comprise a first host tag and a second host tag. In more embodiments, markers can comprise a first barcode sequence with a first host tag, and a second barcode sequence with a second host tag.

An exemplary embodiment of a method for sequencing a template nucleic acid can comprise the following steps: (a) sequence the first barcode sequence using a sequencing primer hybridizing to the first primer site; and (b) sequence the second barcode sequence using a sequencing primer hybridizing to the second primer. The result is two sequence reads that help link the template nucleic acid to its genomic neighbors. Given long enough reads, and short enough library fragments, these two reads can be merged informatically to make one long read that covers the entire fragment. Using the barcode sequence reads and the 9 nucleotide duplicated sequence present from the insertion, reads can now be linked to their genomic neighbors to form much longer "linked reads" in silico.

As will be understood, a library comprising template nucleic acids can include duplicate nucleic acid fragments. Sequencing duplicate nucleic acid fragments is advantageous in methods that include creating a consensus sequence for duplicate fragments. Such methods can increase the accuracy for providing a consensus sequence for a template nucleic acid and/or library of template nucleic acids.

In some embodiments, analysis can involve DNA or RNA or protein, or any combination thereof, from a single cell, or from one or more cellular and/or nuclear compartments. In some embodiments, the analysis is conducted across 10, 100, 1000, 10,000, 100,000, 1,000,000, 10,000,000, 100,000,000, 1,000,000,000 or more cells, or cellular and/or nuclear compartments.

In some embodiments of the sequencing technology described herein, sequence analysis is performed in real time. For example, real time sequencing can be performed by simultaneously acquiring and analyzing sequencing data. In some embodiments, a sequencing process to obtain sequencing data can be terminated at various points, including after at least a portion of a target nucleic acid sequence data is obtained or before the entire nucleic acid read is sequenced. Exemplary methods, systems, and further embodiments are provided in International Patent Publication No. WO 2010/062913, the disclosure of which is incorporated herein by reference in its entirety.

In an exemplary embodiment of a method for assembling short sequencing reads using a linked read strategy, transposon sequences comprising barcodes are inserted into genomic DNA, a library is prepared and sequencing data is obtained for the library of template nucleic acids. Blocks of templates can be assembled by identifying paired barcodes and then larger contigs are assembled. In one embodiment, the assembled reads can be further assembled into larger contigs through code pairing using overlapping reads.

Some embodiments of the sequencing technology described herein include error detection and correction features. Examples of errors can include errors in base calls during a sequencing process, and errors in assembling fragments into larger contigs. As would be understood, error detection can include detecting the presence or likelihood of errors in a data set, and as such, detecting the location of an error or number of errors may not be required. For error correction, information regarding the location of an error and/or the number of errors in a data set is useful. Methods for error correction are well known in the art. Examples include the use of hamming distances, and the use of a checksum algorithm (See, e.g., U.S. Patent Application Publication No. 2010/0323348; U.S. Pat. Nos. 7,574,305; and 6,654,696, the disclosures of which are incorporated herein by reference in their entireties).

In some embodiments, the cellular and/or nuclear proteins may be analyzed, detected, and/or sequenced. In some embodiments, such proteins are uniquely labeled. In some embodiments, the proteins are preserved, embedded, immobilized, or contained within one or more CEs. Identification and sequencing may be performed using methods known in the art. In some embodiments, the identification and or sequencing of the protein can be carried out together with gathering sequence information of the nucleic acids.

In some embodiments, indexing may be performed by generating indexing primers from on-bead oligonucleotides that contain reverse complement sequences of common library adaptors during PCT (see Example 3, below). During PCT, the P7 primer, for example, hybridizes to its complement sequence at the 3' end of the on-bead oligonucleotide, and its extension results in generation of a fully functional indexed oligonucleotide. The amount of indexed oligonucleotide can be specifically controlled by the number of PCR cycles at appropriate annealing temperatures. The synthesized PCR primer then hybridizes to the B15 region of the library fragment that was introduced by transposition allowing amplification to occur. The P7 primer can be biotinylated in order to enrich ATAC-seq fragments post-PCR for sequencing.

Solid Support

Solid supports as described herein may be used for sequencing and analysis. Solid supports may also be used as contiguity preserving elements. A solid support can be two- or three-dimensional and can comprise a planar surface (e.g., a glass slide) or can be shaped. A solid support can include glass (e.g., controlled pore glass (CPG)), quartz, plastic (such as polystyrene (low cross-linked and high cross-linked polystyrene), polycarbonate, polypropylene and poly(methylmethacrylate)), acrylic copolymer, polyamide, silicon, metal (e.g., alkanethiolate-derivatized gold), cellulose, nylon, latex, dextran, gel matrix (e.g., silica gel), polyacrolein, or composites.

Suitable three-dimensional solid supports include, for example, spheres, microparticles, beads, nanoparticles, polymer matrices such as agarose, polyacrylamide, alginate, membranes, slides, plates, micromachined chips, tubes (e.g., capillary tubes), microwells, microfluidic devices, channels, filters, flow cells, structures suitable for immobilizing a nucleic acid, proteins, or cells. A solid support can include planar arrays or matrices capable of having regions that include populations of template nucleic acids or primers. Examples include nucleoside-derivatized CPG and polystyrene slides; derivatized magnetic slides; polystyrene grafted with polyethylene glycol, and the like.

In some embodiments, the solid support comprises microspheres or beads. By "microspheres" or "beads" or "particles" or grammatical equivalents herein is meant small discrete particles, which may be spherical, non-spherical, or irregular in shape. Suitable bead compositions include, but are not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon, as well as any other materials outlined herein for solid supports may all be used. In certain embodiments, the microspheres or beads are magnetic and/or color coded to allow for separation and manipulation. Beads or microspheres may be solid or hollow, and may be porous. Porosity of the beads or microspheres can be tailored as needed by appropriate selection of material and formation method. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller or larger beads may be used.

In some embodiments, the beads can comprise antibodies or other affinity probes (see Immobilized Biomolecules in Analysis. A Practical Approach. Cass T, Ligler F S, eds. Oxford University Press, New York, 1998. pp 1-14, incorporated herein by reference, for typical attachment protocols). In some embodiments, the antibodies can be monoclonal and in other embodiments, the antibodies can be polyclonal. In some embodiments, the antibodies can be specific for a cell surface epitope. In some embodiments, the antibodies can be specific for a protein inside the cell.

In some embodiments, the nucleic acid template provided herein can be attached to a solid support. Various methods well known in the art can be used to attach, anchor, or immobilize nucleic acids to the surface of the solid support.

In some embodiments, the solid support can encapsulate the cell, the cell and cellular and nuclear compartments of the cell, cellular and nuclear compartments of the cell, or nuclear compartments of the cell.

EXAMPLES

The following examples serve to describe but not limit the disclosure provided herein.

Example 1: Tagmentation of Nuclear DNA with Cell-Permeable Clathrin Inhibitor

Using a standard cell culture protocol, 1×10⁶ K562 cells (human lymphoma cell line) were collected from tissue culture flasks for tagmentation reaction. All cell pelleting/centrifugation steps were performed at 300×g for 3 min at 4° C. Freshly isolated cells were centrifuged and re-suspended in ice cold PBS (phosphate-buffered saline). The cells were pelleted again and incubated on ice while being suspended in 200 µL ice cold cell lysis buffer (Tris/NaCl/octylphenoxypolyethoxyethanol (IGEPAL CA-630 detergent)) for 5 min.

Following this, nuclei were spun down for 3 min at 300×g, washed once with 200 of lysis buffer, and pelleted nuclei were transposed with Nextera Tn5 Transposase (TDE1) for 30 min at 55° C. in 1× Tagment DNA buffer (PN:15027866), supplemented with (a) Pitstop-2 in DMSO to yield 30 µM final Pitstop-2 concentration (test nuclei) or (b) 2% DMSO (control nuclei). Nuclei from each sample were pelleted and most of the supernatant was carefully removed.

Example 2. Removal of Transposase from Tagmented DNA with Strand-Displacing Polymerase Tagmented nuclei from the previous example (test and control pools) were re-suspended in Phi29 reaction mixture containing 50 mM Tris-HCl pH 7.5, 10 mM $MgCl_2$, 10 mM $(NH_4)_2SO_4$, 4 mM DTT, 0.005% SDS, 200 µM each dNTP, and 10 units of Phi29 DNA polymerase (New England BioLabs), and the resulting mixture was incubated for 30 min at 30° C. in a thermocycler. Then, nuclei were pelleted by gentle centrifugation in a benchtop strip tube centrifuge and re-suspended in 30% Optiprep (Sigma-Aldrich) in Tris buffer at a final volume of 30 µL.

Figure 3:
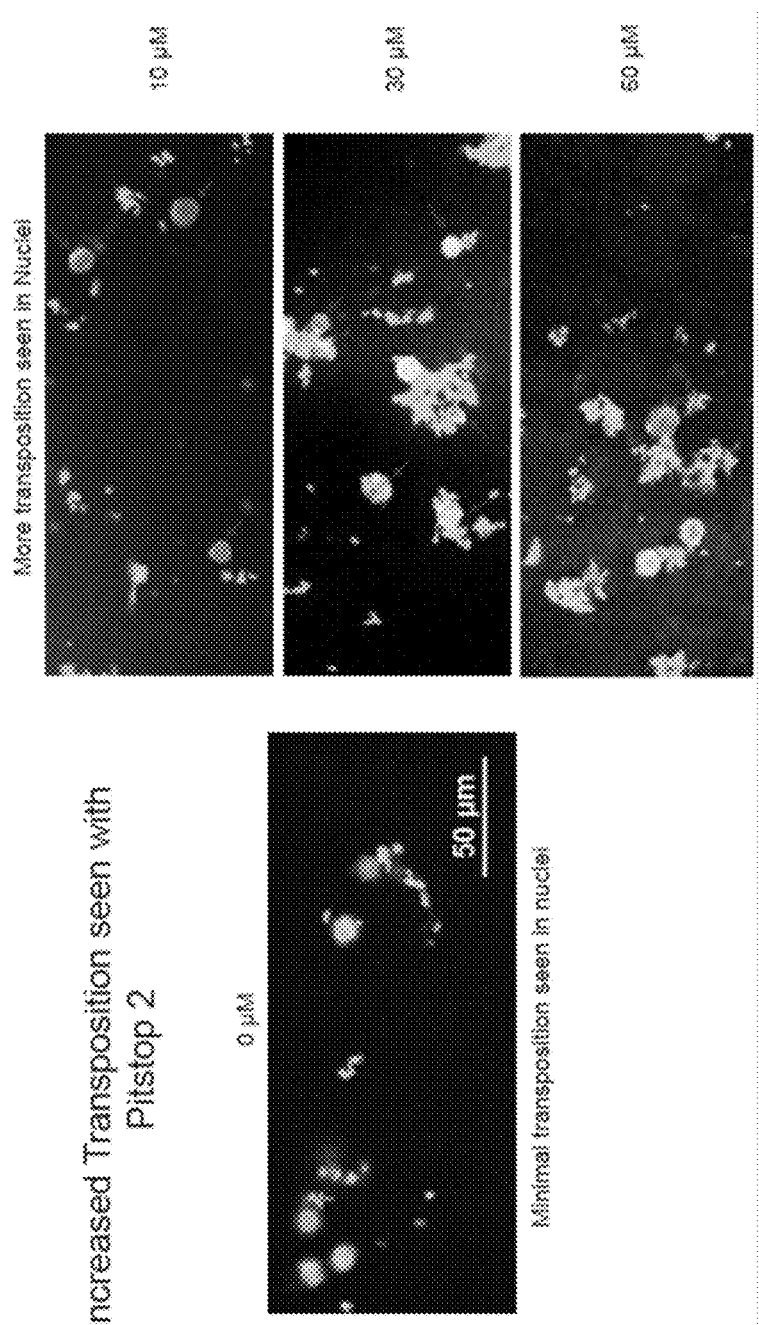
FIG. 3 shows visualization of isolated nuclei treated with FAM-labeled transposome complexes in the presence of varying concentrations of Pitstop-2, as described in Example 3.

Example 3. Visualization of Transposome Access to Nuclei with FAM-Labeled Complexes The method of Example 1 was used to import FAM-labeled transposome complexes into nuclear compartments. Nuclei were isolated and treated as described in Example 1 using Nextera Tn5 transposase complexed with transposon sequence labeled during oligonucleotide synthesis at the 5'-end with FAM (6-FAM, Integrated DNA Technologies), and using the 2% DMSO control, and varying concentrations of Pitstop-2 (10 µM, 30 µM, and 60 µM). As shown in FIG. 3, treatment with Pitstop-2 increased influx of FAM-labeled transposomes into the nuclear space, particularly on the periphery of the nuclei (indicated by arrows).

Example 4. Effect of Pitstop-2 Treatment on DNA Library Generation

Isolated nuclei (50,000) were transposed with the Nextera Tn5 kit as described in the preceding examples in the presence of different concentrations of Pitstop-2 (0 to 80 Excess transposomes were removed by brief centrifugation and the resulting nuclei pellet was treated with Qiagen Protease (ID 19155) for 1 h at 50° C., followed by 10 min at 80° C. The resulting lysate was analyzed with 25 cy qPCR performed in a Bio-Rad Thermocycler with KAPA SYBR Fast master mix and primers annealing to the mosaic end (ME) portion of transposons. Cq values corresponding to different Pitstop-2 concentrations, and Delta Cq between Pitstop-2 samples and control samples (no Pitstop-2) are displayed in Table 1. One Cq value roughly corresponds to two fold difference in DNA Input. As shown in the table, treatment of intact nuclei with Pitstop-2 increases library yield compared to the untreated control. One Cq value roughly corresponds to a two-fold difference in DNA input.

TABLE 1A

Pitstop-2 increases library yield from transposed nuclei

| Pitstop-2 Conc. (uM) | Cq-Pitstop-2 | % DMSO | Cq-DMSO | ΔCq-Pitstop-2 vs. Control |
|---|---|---|---|---|
| 0 | 20.94 | 0 | 20.18 | 0.755 |
| 5 | 19.91 | 0.05 | 20.11 | −0.2 |

TABLE 1A-continued

Pitstop-2 increases library yield from transposed nuclei

| Pitstop-2 Conc. (uM) | Cq-Pitstop-2 | % DMSO | Cq-DMSO | ΔCq-Pitstop-2 vs. Control |
|---|---|---|---|---|
| 10 | 20.00 | 0.10 | 20.64 | −0.65 |
| 20 | 19.36 | 0.20 | 20.84 | −1.48 |
| 40 | 19.94 | 0.40 | 21.20 | −1.26 |
| 80 | 19.24 | 0.80 | 21.30 | −2.06 |

Additional experiments were run using varying concentrations of Pitstop-2 and the Tn5 and TsTn5 transposases. Data for these experiments are shown in Table 1B.

TABLE 1B

| Transposome | Pitstop (µM) | Cq |
|---|---|---|
| Tn5 | 300 | 23.67 |
| Tn5 | 200 | 23.105 |
| Tn5 | 100 | 23.17 |
| Tn5 | 50 | 22.21 |
| Tn5 | 0 | 24.21 |
| TsTn5 | 300 | 19.475 |
| TsTn5 | 200 | 18.55 |
| TsTn5 | 100 | 18.52 |
| TsTn5 | 50 | 18.32 |
| TsTn5 | 0 | 20.97 |

Example 5. Sequencing of Transposition Libraries

Figure 4:
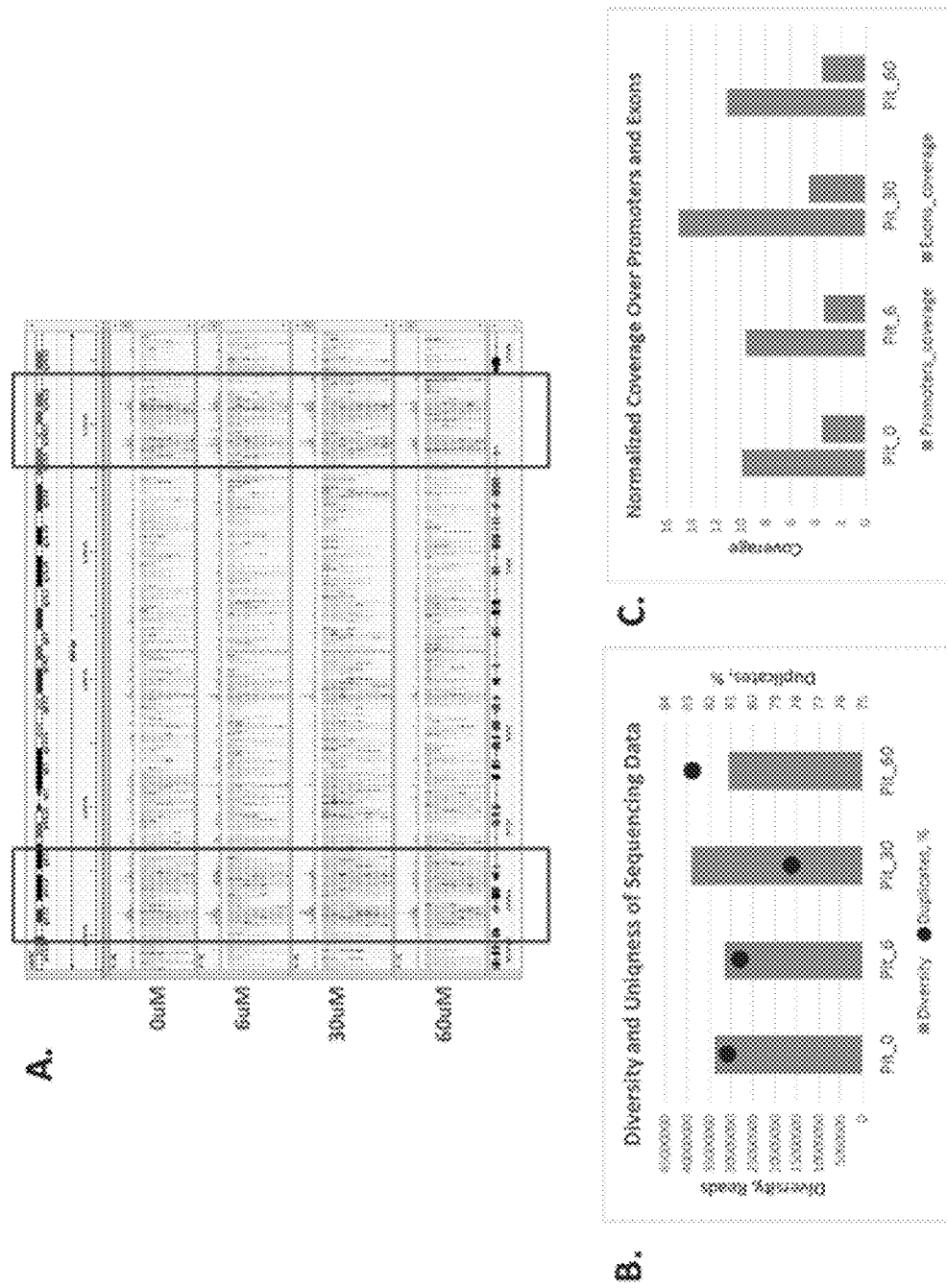
FIGS. 4A, 4B, and 4C show sequencing results for ATAC-seq libraries generated with and without treatment with Pitstop-2, as described in Example 5.

DNA libraries were generated from K562 (human lymphoma cell line) nuclear content using methods as described in the preceding examples. The libraries were sequenced, and the results demonstrated that Pitstop-2 treatment enhanced access to transposase-accessible intergenic and open chromatin regions. As shown in FIG. 4A for the ATAC-seq profile over a portion of Chr 12, the libraries had targeted predominantly intergenic regions at all Pitstop-2 concentrations. As shown in FIG. 4B, a more detailed analysis of sequencing data, showing basic metrics of whole genome sequencing coverage, indicated better diversity and uniqueness for Pitstop-2-treated samples over controls, consistent with improved library yields with Pitstop-2. FIG. 4C shows normalized coverage over promoter and coding regions of the human genome, and the data show that treatment with 30 and 60 µM Pitstop-2 improved the ATAC-seq profile over controls, showing increased coverage over the intergenic region. These results demonstrate that Pitstop-2 treatment enhances access of transposome complexes into nuclei and improve efficiency of nuclear transposition.

Example 6. Indexing of Transposed Nuclear DNA in Presence of Pitstop-2

Figure 5:
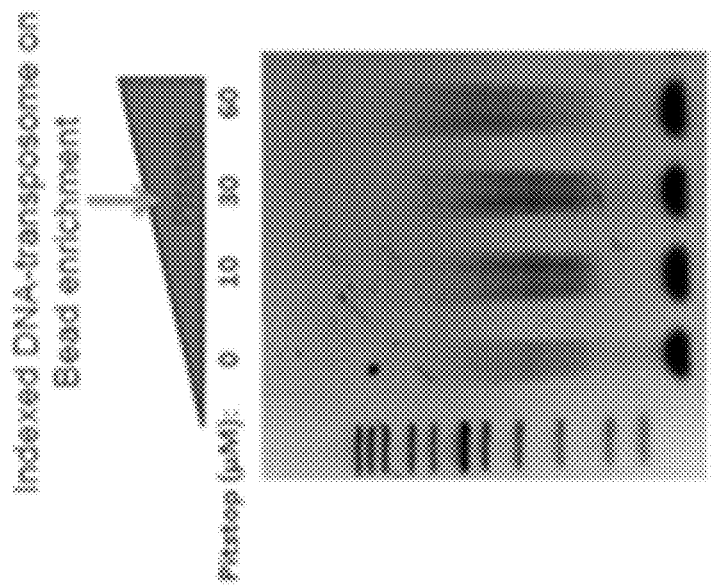
FIG. 5 shows an agarose gel image of transposed DNA libraries made in the presence and absence of Pitstop-2.

Genomic DNA transposed with Nextera Tn5 Kit in the presence of Pitstop-2 (at concentrations of 0, 10, 30, and 60 µM) as described above was released from nuclei and was captured onto indexed beads containing oligonucleotide capture sequences. Bead-captured DNA was further gap-fill ligated to covalently link both strands of genomic DNA to common sequences (including unique indices) and amplified by PCR. When analyzed by agarose gel electrophoresis, the amplified libraries showed a clear increase in transposition yield with the use of Pitstop-2 (FIG. 5). Band intensity increases correlated with increases in Pitsthop-2 concentration. Corresponding DNA fragments covered by distinct number of nucleosomes of resulted libraries contained "nucleosomal banding," indicating successful ATAC-seq tagmentation at regions free of nucleosomes.

In a separate experiment, FAM-labeled transposed nuclear material was obtained from treatment with Pitstop-2 (at concentrations of 0, 10, 30, and 60 using the methods described above, and was enriched on beads with capture oligonucleotides, and the beads were analyzed by flow cytometry to assess capture efficiency. In agreement with the previous results, FAM-labeled transposed libraries prepared with Pitstop-2 treatment exhibited enhanced bead capture rates over control pools (Table 2).

TABLE 2

| Pitstop-2 Concentration | Blank | 0 µM | 10 µM | 30 µM | 60 µM |
|---|---|---|---|---|---|
| Mean (MFU) | 1044 | 1342 | 1297 | 1439 | 1488 |

Example 7. Removal of Transposase by Strand-Displacing Polymerase

In certain transposition library preparation methods, removal of the transposase from the DNA causes further fragmentation of the tagmented DNA. In contrast, removal of the transposase using strand-displacement amplification maintains contiguity of the transposed nuclei and all the single cell related individual libraries of the nuclei.

Figure 6:
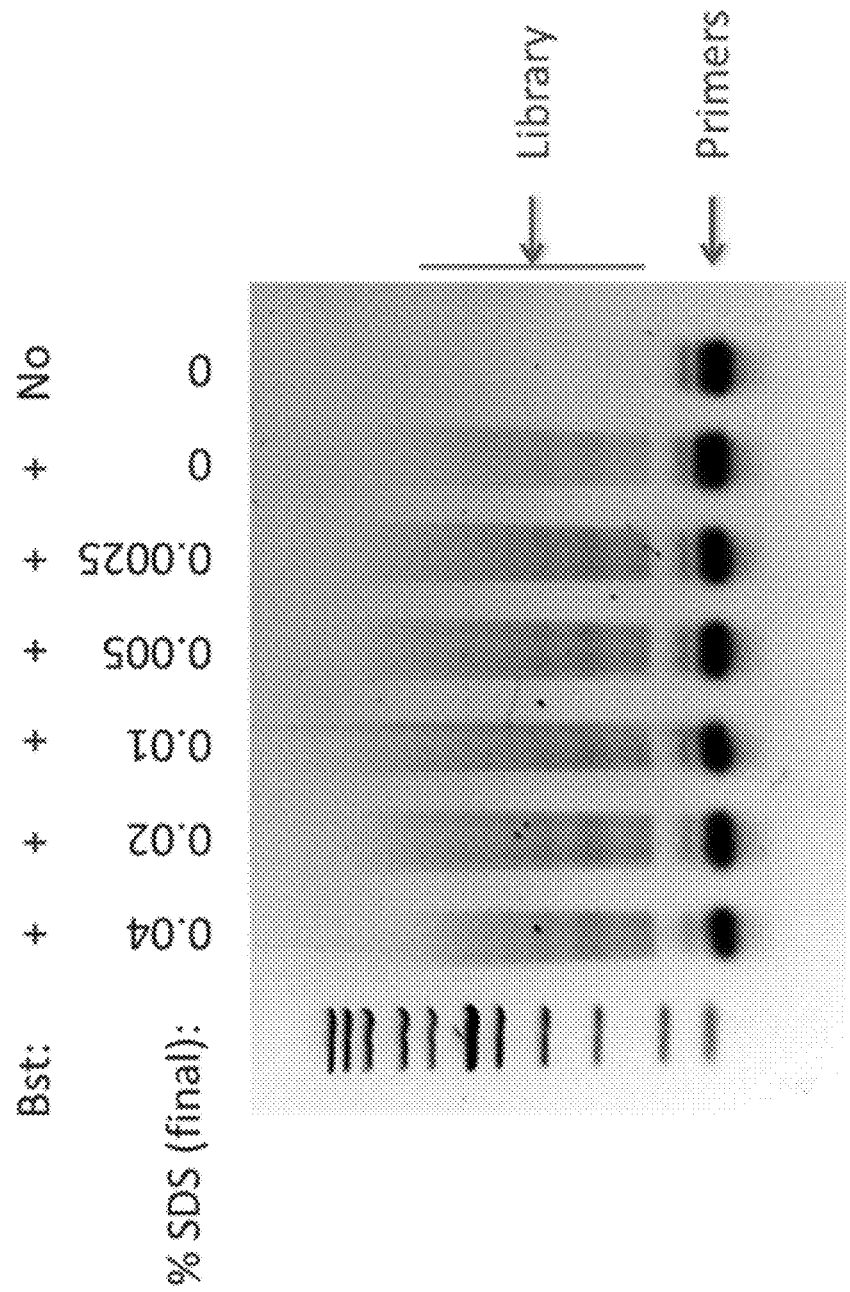
FIG. 6 shows an agarose gel image of ATAC-seq library generation with unpurified, tagmented nuclei after treatment with a strand-displacing polymerase, as described in Example 7.

As an alternative to purification of gDNA after the tagmentation step and prior to amplification, a strand-displacing polymerase may be used to effect transposase removal and amplification in a single step. Unpurified nuclear tagmentation product in intact nuclei (24 ng), prepared as described in the preceding examples in the presence of 30 µM Pitstop-2, was treated with Illumina NPM PCR master mix, a strand-displacing polymerase (Bst), and a low concentration of SDS (0.0025%-0.04%). As shown in FIG. 6, the addition of Bst improved amplification efficiency of tagmented DNA.

In further experiments, sequencing libraries were generated from transposed, pelleted nuclei using a strand-displacing polymerase to remove the transposase from the tagmented DNA. No sequencing libraries were observed in the supernatant after strand-displacement amplification, demonstrating that no DNA fragments were "leaking" into the supernatant from the nuclei. Nuclei can be used as "compartments" to perform reactions and assay steps without losing contiguity information about the state of bordering or in direct contact of components of the single cell.

Example 8. Yield of ATAC-Seq Library from Unpurified Nuclei

Figure 7A:
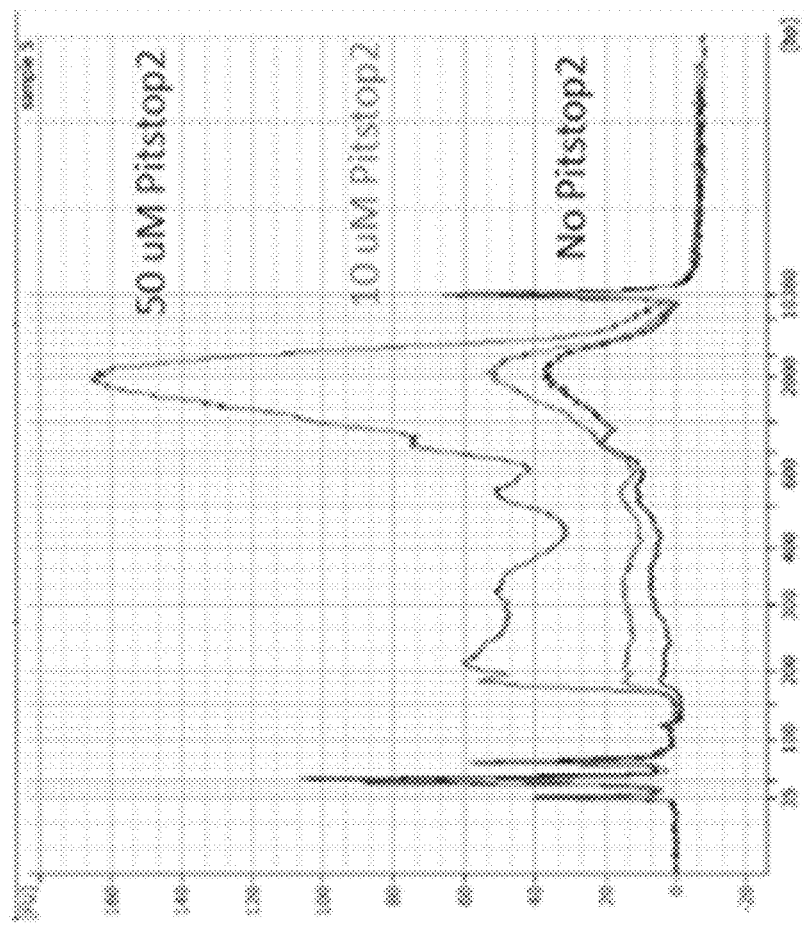
FIGS. 7A and 7B show the results described in Example 8.

Treatment of nuclei with Pitstop-2 (10 and 100 µM) as described in the preceding examples increased the yield of an ATAC-seq library generated from unpurified nuclei samples as shown by analysis of 1 µL of each ATAC-seq library on a high-sensitivity chip on a BioAnalyzer instrument. The concentration of each library was determined on the BioAnalyzer between the library range of 150-1000 bps plotted for each Pitstop-2 concentration (FIG. 7A). Additional experiments run at varying Pitstop-2 concentrations (5, 10, 30, 50, 100, and 200 µM) produced enhanced library yield over libraries produced in the absence of Pitstop-2 as shown by spectrophotometric analysis (Table 3).

TABLE 3

| Pitstop-2 Concentration (µM) | % DMSO | Yield (nM) 150-1000 bp |
|---|---|---|
| 0 | 3 | 2.9 |
| 5 | 3 | 7.3 |
| 10 | 3 | 9.3 |
| 20 | 3 | 20.6 |
| 50 | 3 | 23.7 |
| 100 | 3 | 15.7 |
| 200 | 3 | 8.7 |

Figure 7B:
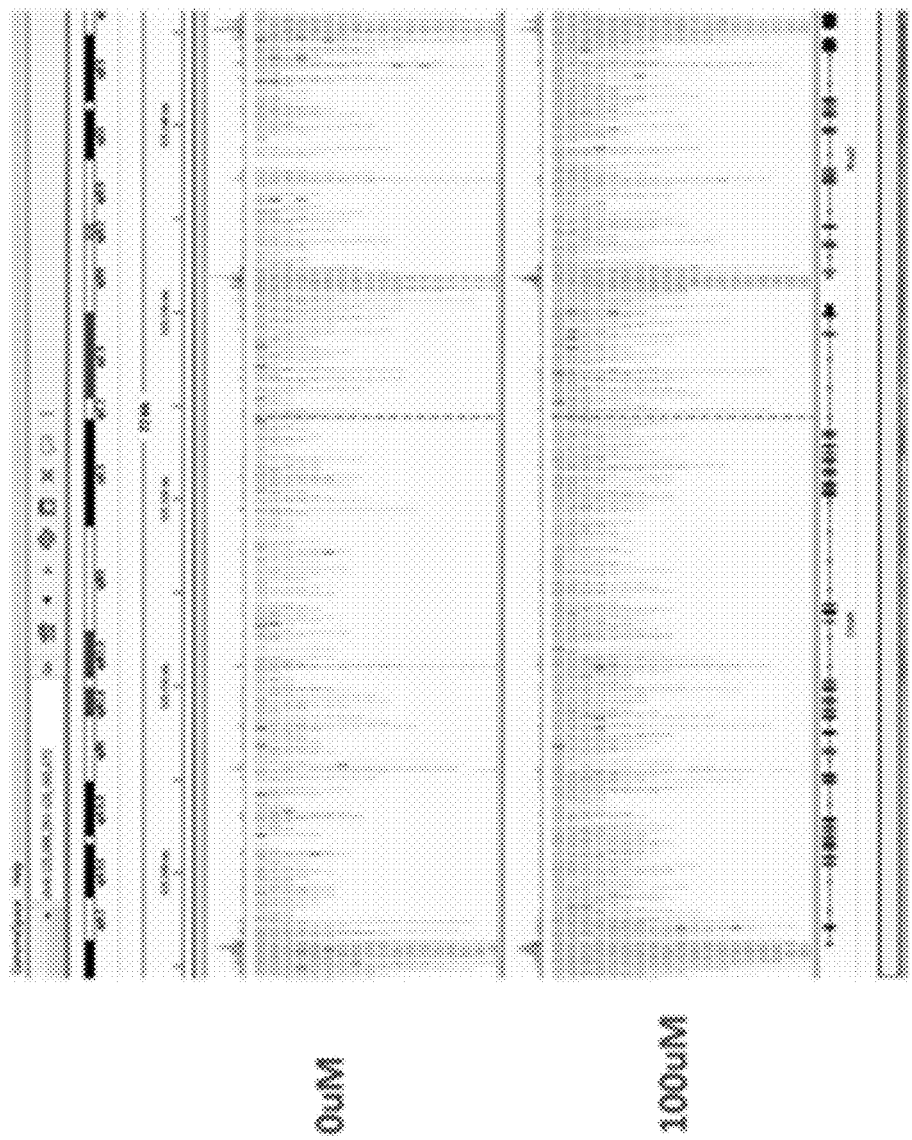

FIG. 7B shows the ATAC-seq profile over a portion of Chr 6 for studies using 0 and 100 µM Pitstop-2.

Example 9. RNA Output from Nuclei

Pitstop-2 treatment increases RNA output by improving cDNA synthesis from nuclear mRNA. K562 cells were lysed with 0.1% NP40. The nuclei and cytoplasm were separated and the nuclei were washed twice, then a reverse transcription/quantitative PCR protocol was performed (ThermoFisher Maxima HT RT kit, Kapa qPCR kit, RPLPO PCR primer) with (a) no additive, (b) 0.1% SDS, or (c) 30 µM Pitstop-2. The deltaCt between no reverse transcription and reverse transcription was used as the metric to report relative cDNA synthesis efficiency. Pitstop-2 treatment boosted cDNA synthesis from nuclei 4-5 fold over untreated nuclei (Table 4).

TABLE 4

| Run | DeltaCt |
|---|---|
| Cytoplasm | 8.84 |
| Nuclei (Untreated) | 4.63 |
| Nuclei (+0.1% SDS) | 2.47 |
| Nuclei (+30 µM Pitstop-2) | 7.19 |

Example 10: Preparation of Indexed Beads

Surface functionalized beads to enable oligonucleotide coupling (e.g., hydrazine-aldehyde, epoxide-amine, etc.) of 30 µm diameter and $1 \times 10^7$ bead density were washed in deionized $H_2O$. The washed beads were added to each well of a 96 well plate at a concentration of $1 \times 10^5$ beads/50 µL. Following this, 500 pmoles of unique 5' aldehyde indexing oligo_1 (/5FormInd/CCGAGCCCACGAGAC (SEQ ID NO: 10) INDEX1 GACTTGTC) was added into each well respectively to a final volume of 50 µL of reaction mixture per well. The plate was sealed to avoid evaporation and incubated overnight at 37° C. in a rotary incubator. Beads were pooled and washed three times with 0.1×TE/0.1% Tween-20. Washed beads were distributed the same way as described earlier to individual wells of a 96 well plate to which unique 5' phosphorylated index oligo_2 (/5Phos/TAGAGCAT INDEX2 ATCTCGTATGCCGTCTTCTGCTTG (SEQ ID NO: 11)), splint oligo was added along with T4 DNA ligase suspended in T4 DNA ligase buffer. Ligation reaction was allowed to proceed overnight at room temperature. The beads were then finally pooled together from all wells and washed three times with 0.1×TE/0.1% Tween-20.

Example 11. "On the Fly" Index Primer Generation

Figure 8:
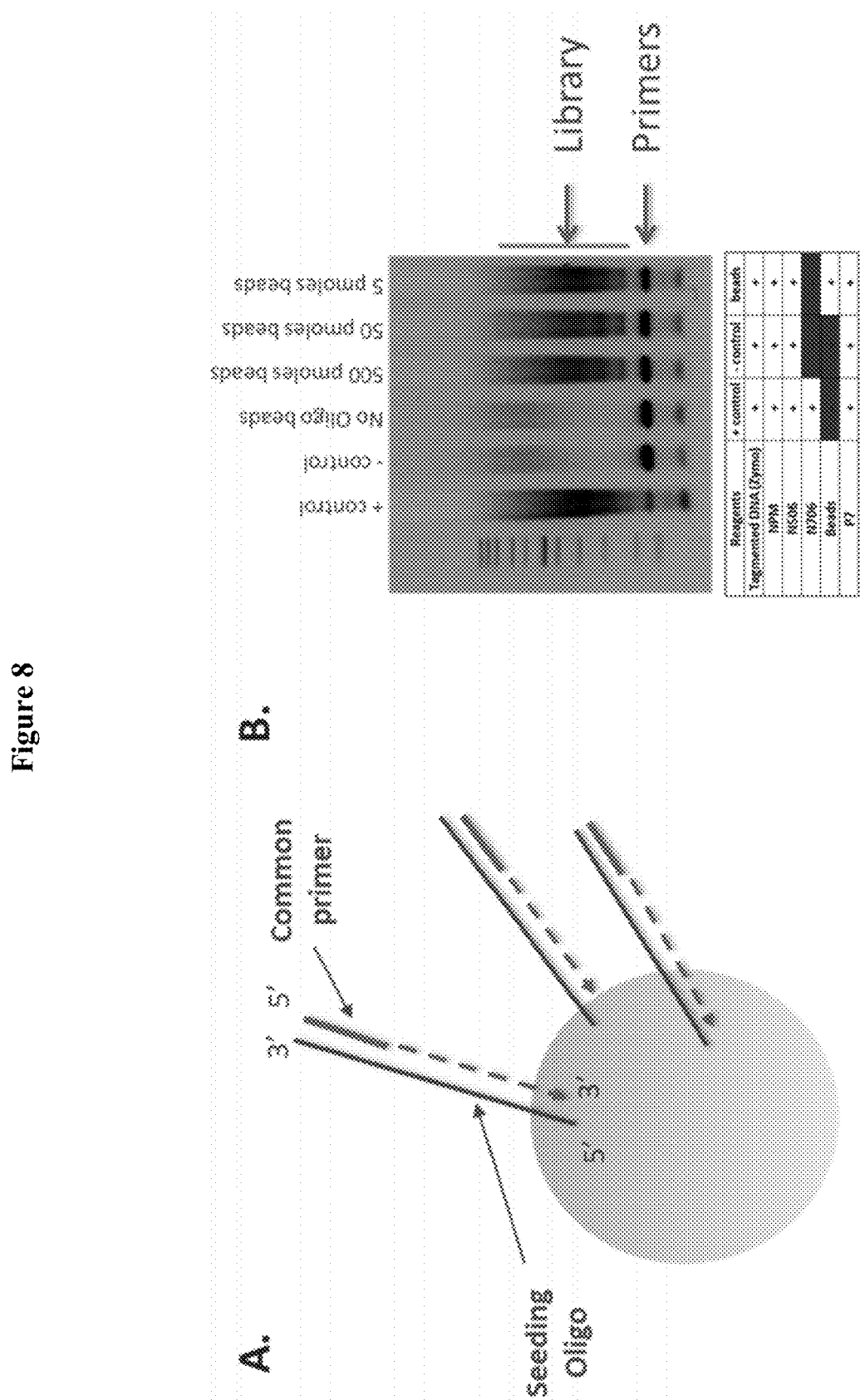
FIGS. 8A and 8B describe index primer generation as discussed in Example 11.

Performing indexing during PCR either with a mixture of nuclei or in droplets requires a panel of individually indexed PCR primers, presented on combinatorially synthesized beads. These primers can be either cleaved from the beads before being used in PCR or can be oligonucleotide ("seeding oligo") with a reverse complimentary sequence of actual PCR primers. In the latter case, a common primer (for example P5 or P7) in a PCR mixture would hybridize to the indexed "seeding oligo" on the bead and produce an indexed primer used in PCR. Density of the "seeding oligo" can be adjusted to optimize PCR, and each round of PCR will generate an additional amount of indexed PCR primer. As shown in FIG. 8A, a seeding oligo with a reverse complementary sequence to indexed PCR primer is coupled to a bead. PCR mixture is supplemented with a common primer, which anneals to the "seeding oligo" and, upon extension in each PCR cycle, generates a primer used for library amplification.

In one experiment, conjugated beads containing the indexing oligo (B15', nuclei index, P7') having the reverse complement of P7 on its 3' end were added to a PCR master mix at 250 beads/µL. The master mix composed of Nextera PCR Master Mix (NPM), 0.01% SDS, 0.5 µM sample indexing primer (P5, sample index, and A14'), 0.5 µM P7 primer, and 30% Optiprep was added to well 1 on a drop generator chip. Nuclei ($6 \times 10^4$) were added to well 2 along with 250 beads/µL suspended in 30% Optiprep. Indexing primers were generated from the on-bead oligo during PCR upon hybridization of P7 to its 3' end, extension, and denaturing off the bead. The P7 primer can also be biotinylated in order to enrich ATAC-seq fragments post-PCR for sequencing. The synthesized PCR primer then hybridizes to the B15 region of the library fragment produced by transposition, thus allowing amplification to occur. The following PCR parameters were followed: initial extension at 73° C. for 3 min, 98° C. for 30 sec, 25 cycles of 98° C. for 10 sec, 56° C. for 30 sec, and 73° C. for 30 sec.

In other experiments, seeding oligonucleotides were affixed at different concentrations to the beads and these beads were used in PCR as a source of one of the PCR primers, side by side with a positive control, containing both PCR primers, and a negative control with only one PCR primer. As presented in FIG. 8B, libraries generated with beads with coupled "seeding oligo" provide sufficient amount of second PCR primer to support efficient amplification. FIG. 6B shows amplification of libraries with either two PCR oligonucleotides (+ control), or one PCR oligonucleotide and beads with seeding oligonucleotide (5, 50, and 500 pmol beads), and the reagents used in the experiments.

Example 12. Droplet Generation

Droplets were generated using a QX200 Bio-Rad droplet generator comprising a cell, bead, and oil inlets. Briefly, 10 µL of the priming solution (such as aqueous buffer or cell media) was added into a cell inlet and a bead inlet and allowed to fill the channels for 1 min, and was then removed. Nuclei and bead solutions (30 µL of each) were added to respective wells. Approximately 70 µL of oil was added to each oil inlet prior to inserting the cartridge into the droplet generator. After droplet generation, the droplets were pooled together from both the outlets and PCR was performed. After PCR, the water-in-oil emulsion was broken by treatment with emulsifier, and the aqueous phase was used for sequencing.

Example 13. Nuclei as Physical Compartments for Enzymatic Reactions

Living cells have multiple organelles which harbor different machineries to perform separate enzymatic reactions, such as genome maintenance in the nucleus, energy production in mitochondria, catabolic processes in the lysosome, etc. To utilize the natural compartmentalization provided by living cells, experiments were performed that illustrate that the nucleus can provide the physical barrier for isolated in vitro reactions of genomic DNA.

Nuclei (150,000) were extracted with standard nuclei isolation buffer containing 0.1% IGEPAL CA-630 and nuclear pellets were transposed with Tn5 transposome with and without 30 µM Pitstop-2 for 30 min at 55° C. The integrity of the nuclei on completion of this step was monitored by light microscopy (data not shown). Nuclei were pelleted with gentle centrifugation and excess unused transposomes were removed. Nuclei were re-suspended in a reaction mixture containing a strong strand-displacing DNA polymerase (Bst or Phi29) and incubated at appropriate temperatures (65 C, Bst; 30 C, Phi29) for 30 min to remove Tn5 from tagmented chromatin and to make DNA fragments available for PCR amplification. After the reaction was completed, nuclei were separated from the supernatant by gentle centrifugation and re-suspended in PCR master mix.

Figure 9:
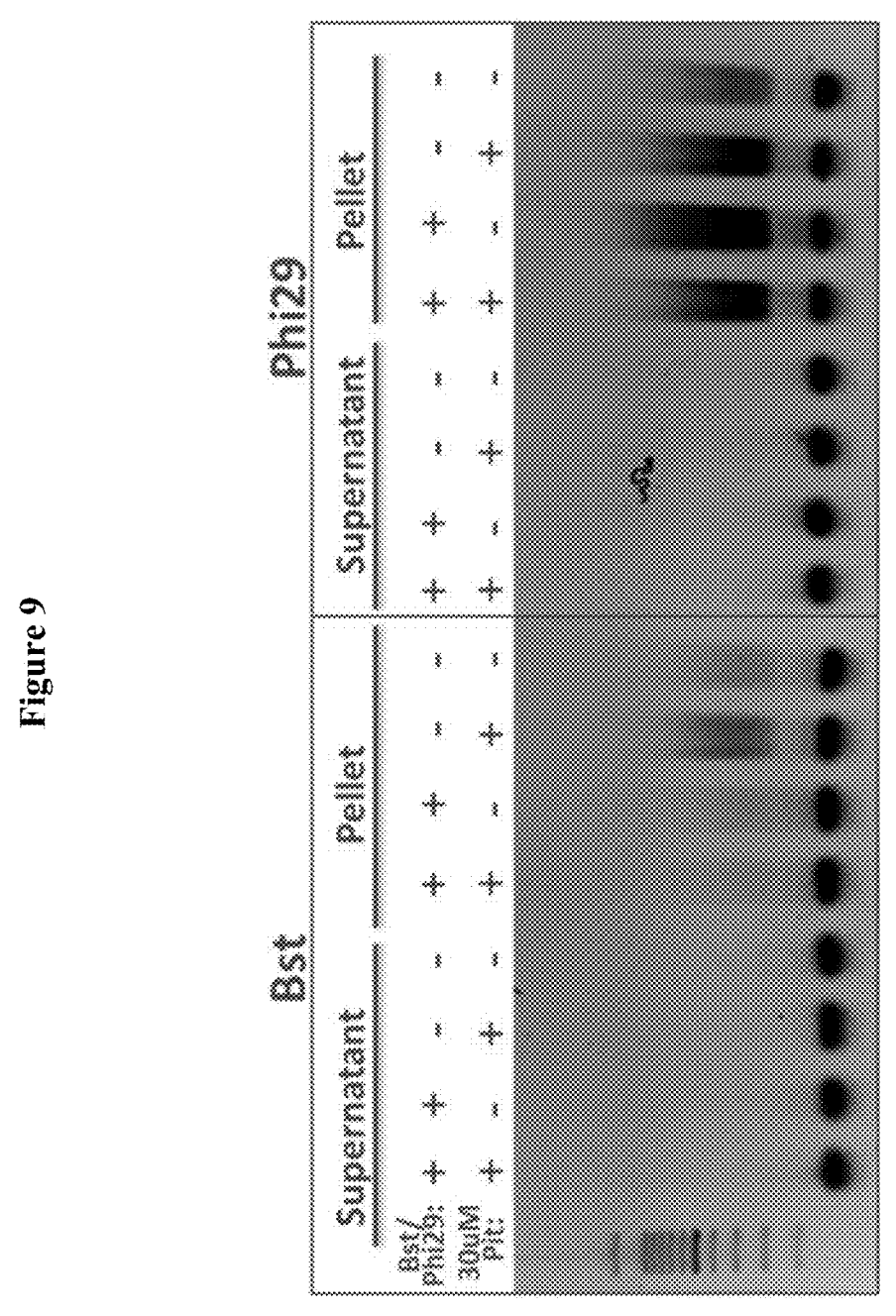

Both nuclei and supernatant were amplified (25 cycles) with Nextera index kit primers, and the products of the reactions were analyzed by agarose gel electrophoresis as shown in FIG. 9. No library was generated from the supernatant under either set of conditions, suggesting that DNA fragments did not diffuse out of the nuclei during tagmentation and Tn5 displacement reactions.

Figure 10:
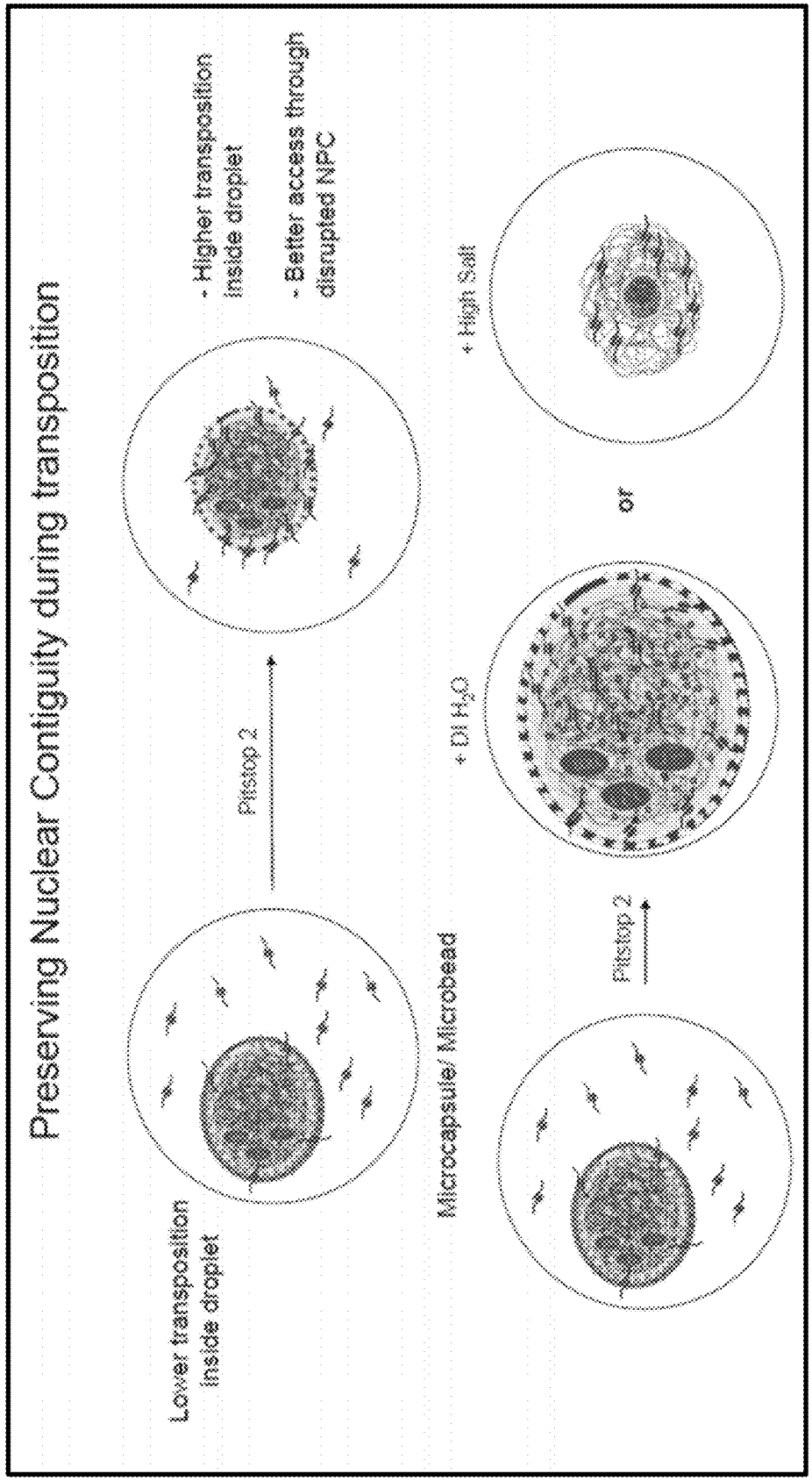
FIG. 10 is a schematic of use of the nuclear membrane as a CE for transposition, along with further methods that expose the transposed nuclei to deionized water or high salt conditions.

The data show that nuclei are used successfully as physical compartments for tagmentation and other enzymatic processes (see FIGS. 1, 2, and 10). Thus, the present methods effect compartment-specific amplification of in-nuclei transposed products. Enzymes, such as the Tn5 transposome complex and polymerases, as well as other reaction mixture components, are able to enter and function within nuclei treated with Pitstop-2. DNA and library elements remain in the nuclei during and post-reaction. Multiple enzymatic reactions can therefore be accomplished within the nuclei without disrupting the integrity of the nuclear membrane, and nuclei can be subject to multiple reagent exchanges, multiple processes, and/or various manipulations (e.g., enzymatic reactions, staining, sorting, etc.) without DNA leakage from the nuclear space.

Example 14. Effect of Pitstop-2 on Single-Cell ATAC-Seq Metrics in Droplets

Figure 11A:
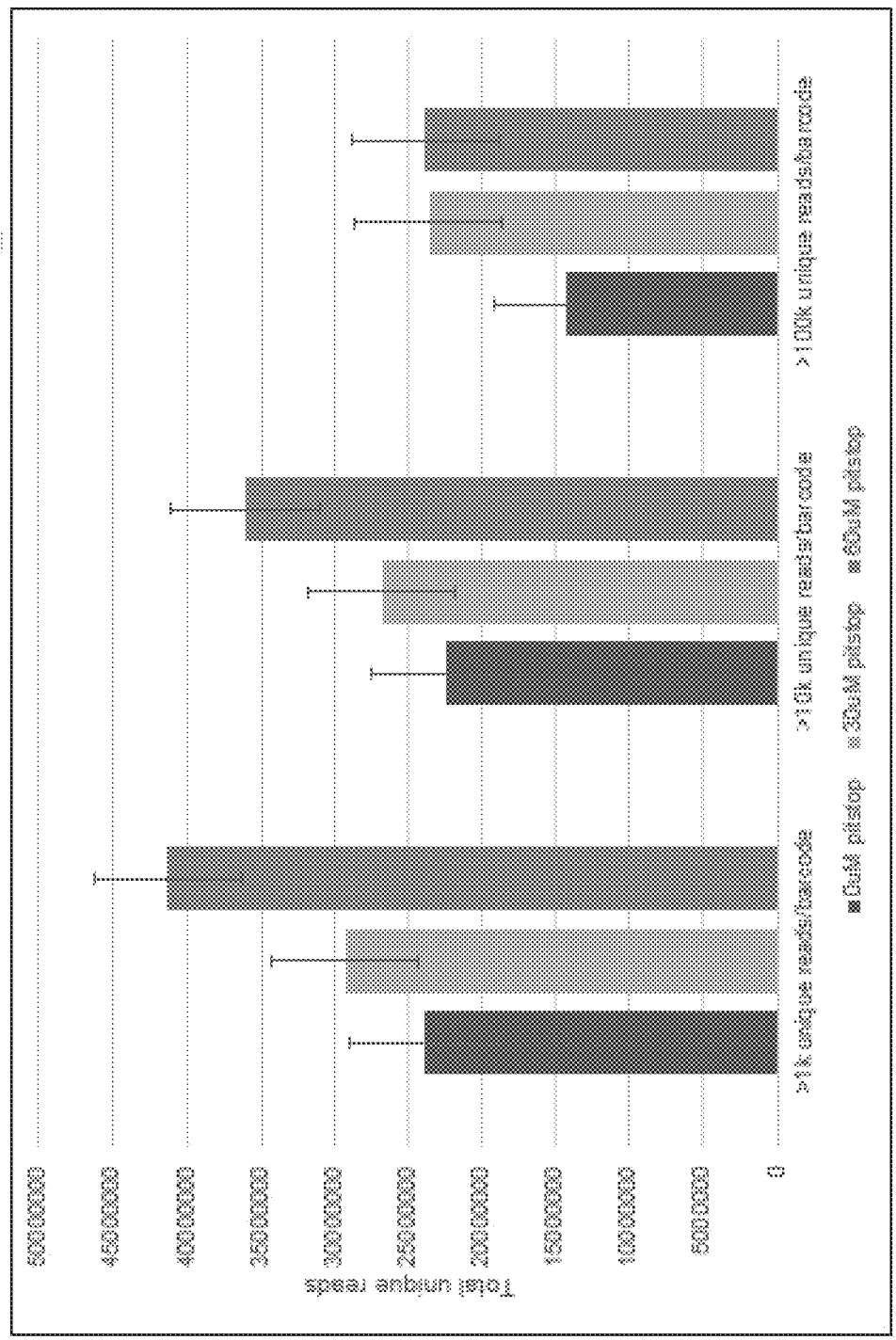
FIG. 11A shows the effect of Pitstop-2 concentration on total number of unique reads for three sets of barcodes grouped by different number (>1 k, >10 k and >100 k) of unique reads.

Mouse (3T3) nuclei were treated with 0 µM, 30 µM, and 60 µM Pitstop-2 during cell lysis and transposition of nuclei. Pitstop-2 was used to open up nuclear pores and to allow increased transposition of open chromatin. A defined number of transposed nuclei set to ensure single nuclei occupancy was loaded into a QX200 Bio-Rad droplet generator with indexed beads designed to produce single-cell ATAC-seq libraries. Single cell libraries were PCR-amplified in droplets and then subjected to purification, and sequencing on a NextSeq® 550 Sequencing System. FIG. 11 shows single-cell sequencing data for each set of treated cells (0 µM, 30 µm, and 60 µM Pitstop-2). As shown in FIG. 11A, increasing the concentration of Pitstop-2 resulted in an increase in the total number of unique reads for all three sets of barcodes grouped by different number (>1 k, >10 k and >100 k) of unique reads.

Figure 11C:
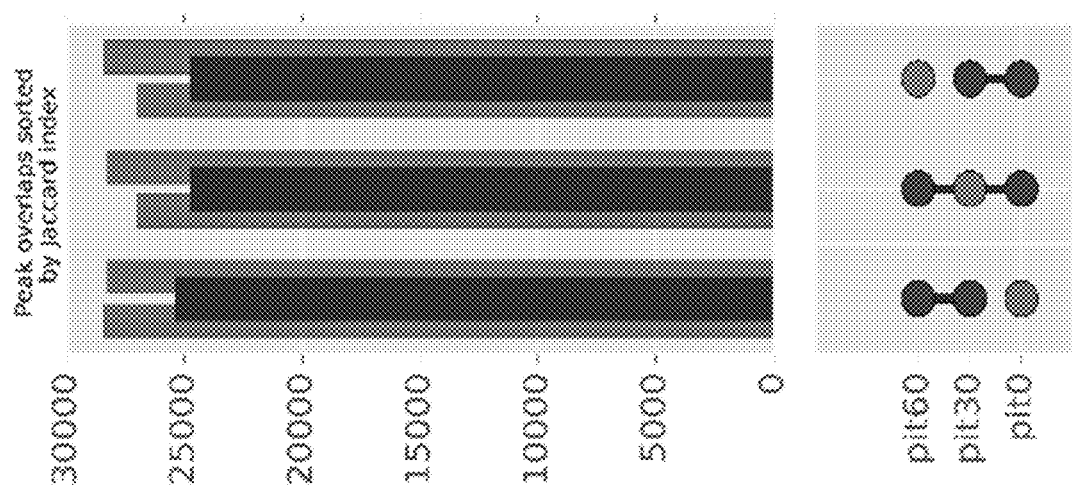
FIG. 11C shows ATAC-seq peak overlaps defined by MACS-2 peak finding program for samples treated with 0 μM, 30 μM, and 60 μM Pitstop-2.

Treatment of nuclei with Pitstop-2 allows more efficient transposition and increased unique coverage of open chromatin. In the presence of Pitstop-2, transposases target additional open chromatin regions outside of transcription start sites (TSS) (see FIG. 11B). FIG. 11B shows the percentage of fragments for ATAC seq samples with 0 µM, 30 µM, or 60 µM Pitstop-2 within 1 kb of transcription start sites. Detailed examination of reads alignment at two genomic locations (GAPDH and RPL10 genes) indicated library generation at regions with potentially open chromatin structure such as enhancers and open reading frames, suggesting higher sensitivity of the assay (data not shown). FIG. 11C shows ATAC-seq peak overlaps defined by the more conservative MACS-2 peak finding software program for samples treated with 0 µM, 30 µM, and 60 µM Pitstop-2. A very strong peak overlap was detected for samples with and without Pitstop-2, indicating that Pitstop-2 did not change the overall integrity of the assay (see FIG. 11C). Also observed were an alignment of pooled ATAC-seq reads generated with 0 µM, 30 µM, and 60 µM Pitstop-2 around GAPDH gene at chromosome 6 and an alignment of pooled ATAC-seq reads generated with 0 µM, 30 µM, and 60 µM Pitstop-2 around RPL10 gene at chromosome X (data not shown).

The invention claimed is:

1. A method of reacting a nuclear target nucleic acid with a transposome complex, comprising: (a) contacting a cell nucleus comprising the nuclear target nucleic acid with an aliphatic alcohol chosen from trans-1,2-cyclohexanediol, n-hexane-1,2-diol, and 1,6-hexane-diol and reacting a transposome complex with the nuclear target nucleic acid, wherein reacting comprises fragmenting the nuclear target nucleic acid into double-stranded nucleic acid fragments, each having a 3' end and a 5' end, and (b) tagging the double-stranded nucleic acid fragments with the first adaptor sequence at the 5' end of the first strand of the double-stranded nucleic acid fragments and the second adaptor sequence at the 5' end of second strand of the double-stranded nucleic acid fragments to form tagged double-stranded nuclear nucleic acid fragments, wherein the transposome complex comprises: (i) a transposase enzyme, (ii) a first transposon end composition comprising a first transposon end sequence comprising a first adaptor sequence, and (iii) a second transposon end composition comprising a second transposon end sequence comprising a second adaptor sequence, and wherein the transposase enzyme is non-covalently bound to the first transposon end composition and the second transposon end composition.

2. The method of claim 1, wherein the transposome complex further comprises a fluorescein label, thereby delivering a fluorescein-labeled transposome complex into the cell nucleus.

3. The method of claim 2, wherein the fluorescein label is a fluorescein amidite (FAM) label.

4. The method of claim 3, further comprising isolating the cell nucleus treated with FAM-labeled transposome complex in the presence of the aliphatic alcohol chosen from trans-1,2-cyclohexanediol, n-hexane-1,2-diol, and 1,6-hexane-diol.

5. The method of claim 3, further comprising visualizing the cell nucleus treated with FAM-labeled transposome complexes in the presence of the aliphatic alcohol chosen from trans-1,2-cyclohexanediol, n-hexane-1,2-diol, and 1,6-hexane-diol.

\* \* \* \* \*

SEQUENCE LISTING

```
<160> NUMBER OF SEQ ID NOS: 11

<210> SEQ ID NO 1
<211> LENGTH: 7
<212> TYPE: PRT
<213> ORGANISM: Simian virus 40

<400> SEQUENCE: 1

Pro Lys Lys Lys Arg Lys Val
1               5

<210> SEQ ID NO 2
<211> LENGTH: 16
<212> TYPE: PRT
<213> ORGANISM: Unknown
<220> FEATURE:
<223> OTHER INFORMATION: Nucleoplasmin NLS peptide

<400> SEQUENCE: 2

Lys Arg Pro Ala Ala Thr Lys Lys Ala Gly Gln Ala Lys Lys Lys Lys
1               5                   10                  15

<210> SEQ ID NO 3
<211> LENGTH: 19
<212> TYPE: PRT
<213> ORGANISM: Unknown
<220> FEATURE:
<223> OTHER INFORMATION: Nucleoplasmin NLS peptide

<400> SEQUENCE: 3

Ala Val Lys Arg Pro Ala Ala Thr Lys Lys Ala Gly Gln Ala Lys Lys
1               5                   10                  15

Lys Leu Asp

<210> SEQ ID NO 4
<211> LENGTH: 25
<212> TYPE: PRT
<213> ORGANISM: Unknown
<220> FEATURE:
<223> OTHER INFORMATION: EGL-13 NLS peptide

<400> SEQUENCE: 4

Met Ser Arg Arg Arg Lys Ala Asn Pro Thr Lys Leu Ser Glu Asn Ala
1               5                   10                  15

Lys Lys Leu Ala Lys Glu Val Glu Asn
            20                  25

<210> SEQ ID NO 5
<211> LENGTH: 9
<212> TYPE: PRT
<213> ORGANISM: Unknown
<220> FEATURE:
<223> OTHER INFORMATION: c-Myc NLS peptide

<400> SEQUENCE: 5
```

```
Pro Ala Ala Lys Arg Val Lys Leu Asp
1               5
```

<210> SEQ ID NO 6
<211> LENGTH: 9
<212> TYPE: PRT
<213> ORGANISM: Unknown
<220> FEATURE:
<223> OTHER INFORMATION: TUS-protein NLS peptide

<400> SEQUENCE: 6

```
Lys Leu Lys Ile Lys Arg Pro Val Lys
1               5
```

<210> SEQ ID NO 7
<211> LENGTH: 5
<212> TYPE: PRT
<213> ORGANISM: Unknown
<220> FEATURE:
<223> OTHER INFORMATION: Yeast NLS peptide

<400> SEQUENCE: 7

```
Lys Ile Pro Ile Lys
1               5
```

<210> SEQ ID NO 8
<211> LENGTH: 29
<212> TYPE: DNA
<213> ORGANISM: Artificial Sequence
<220> FEATURE:
<223> OTHER INFORMATION: Synthetic primer

<400> SEQUENCE: 8
aatgatacgg cgaccaccga gatctacac                                    29

<210> SEQ ID NO 9
<211> LENGTH: 24
<212> TYPE: DNA
<213> ORGANISM: Artificial Sequence
<220> FEATURE:
<223> OTHER INFORMATION: Synthetic primer

<400> SEQUENCE: 9
caagcagaag acggcatacg agat                                         24

<210> SEQ ID NO 10
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 10
ccgagcccac gagac                                                   15

<210> SEQ ID NO 11
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 11
atctcgtatg ccgtcttctg cttg                                         24